(12) United States Patent
Martin et al.

(10) Patent No.: US 7,214,519 B2
(45) Date of Patent: May 8, 2007

(54) SCREENING METHOD FOR IDENTIFYING HEME INDEPENDENT MODULATORS OF SOLUBLE GUANYLYL CYCLASE (SGC) ACTIVITY USING $\alpha\beta^{CYS105}$ MUTANT SGC

(75) Inventors: Emil Martin, Houston, TX (US); Ferid Murad, Houston, TX (US)

(73) Assignee: Board of Regents of the University of Texas System, Austin, TX (US)

( * ) Notice: Subject to any disclaimer, the term of this patent is extended or adjusted under 35 U.S.C. 154(b) by 361 days.

(21) Appl. No.: 10/777,008

(22) Filed: Feb. 11, 2004

(65) Prior Publication Data

US 2004/0235079 A1 Nov. 25, 2004

Related U.S. Application Data

(60) Provisional application No. 60/446,427, filed on Feb. 11, 2003.

(51) Int. Cl.
*C12N 9/00* (2006.01)
(52) U.S. Cl. .............................. 435/183; 435/4; 435/15
(58) Field of Classification Search ................... 435/4, 435/15, 183
See application file for complete search history.

(56) References Cited

U.S. PATENT DOCUMENTS

2002/0155166 A1   10/2002   Choi et al.
2005/0112717 A1*  5/2005    Buettner ...................... 435/25

OTHER PUBLICATIONS

Abrams, J., Beneficial actions of nitrates in cardiovascular disease. *Am J Cardiol*, 1996. 77(13): p. 31C-7C.
Deinum, G., et al., Binding of Nitric Oxide and Carbon Monoxide to Soluble Guanylate Cyclase as Observed with Resonance Raman Spectroscopy. (1996) *Biochemistry* 35 (5), 1540-7.
Do, Y.S., et al., In-Stent Restenosis Limitation With Stent-Based Controlled-Release Nitric Oxide: Initial Results in Rabbits. *Radiology*, 2004. 230(2): p. 377-82.
Evans, C.H., et al., Osteoarthritis gene therapy. *Gene Ther*, 2004. 11(4): p. 379-89.
Friebe, A., and Koesling, D., Mechanism of YC-1-Induced Activation of Soluble Guanylyl Cyclase. (1998) *Mol Pharmacol* 53 (1), 123-7.
Gallo, O., et al., Role of Nitric Oxide in Angiogenesis and Tumor Progression in Head and Neck Cancer. *J Nat'l Cancer Inst*, 1998. 90(8): p. 587-96.
Lee, Y. C., et al., Human Recombinant Soluble Guanylyl Cyclase: Expression, Purification, and Regulation. (2000) *Proc Nat'l Acad Sci USA* 97(20), 10763-8.
Martin, E., et al., YC-1 Activation of Human Soluble Guanylyl Cyclase has Both Heme Dependent and Heme Independent Components. PNAS. *Proc Nat'l Acad Sci USA* (Nov. 6, 2001) 98 (23), 12938-42.

Okawa, H., et al., Preischemic Infusion of Alpha-Human a Trial Natriuretic Peptide Elicits Myoprotective Effects Against Ischemia Reperfusion in Isolated Rat Hearts. *Mol Cell Biochem*, 2003. 248(1-2): p. 171-7.
Sinnaeve, P., et al., Overexpression of a Constitutively Active Protein Kinase G Mutant Reduces Neointima Formation and In-Stent Restenosis. *Circulation*, 2002. 105(24): p. 2911-6.
Stasch, J. P., et al., Pharmacological actions of a Novel NO-Independent Guanylyl Cyclase Stimulator, BAY 41-8543: *in vitro* Studies. (2002) *Br J Pharmacol* 135 (2), 333-43.
Stasch, J., et al., NO and Haem Independent Activation of Soluble Guanylyl Cyclase: Molecular Basis and Cardiovascular Implications of a New Pharmacological Principle. *British J of Pharmacology* (2002) vol. 136, No. 5, pp. 773-783.
Stone. J. R., et al., Spectral and Ligand-Binding Properties of an Unusual Hemoprotein, the Ferric Form of Soluble Guanylate Cyclase. *Biochemistry* (1996), 35, 3258-62.
Sunahara, R. K., et al., Exchange of Substrate and Inhibitor Specificities between Adenylyl and Guanylyl Cyclases. (1998) *J Biol Chem*. 273 (26), 16332-8.
Takahashi, M., et al., Cyclic GMP Production by ANP, BNP, and NO During Worsening and Improvement of Chronic Heart Failure. *Jpn Heart J*, 2003. 44(5): p. 713-24.
Tomita, T., et al., Effects of GTP on Bound Nitric Oxide of Soluble Guanylate Cyclase Probed by Resonance Raman Spectroscopy. (1997) *Biochemistry* 36 (33), 10155-60.
Wedel, B., et al., Functional Domains of Soluble Guanylyl Cyclase. (1995) *J Biol Chem* 270 (42), 24871-5.
Zhao, Y., and Marietta, M. A., Localization of the Heme Binding Region in Soluble Guanylate Cyclase. (1997) *Biochemistry* 36 (50), 15959-64.
Zhao, Y., et al., Identification of Histidine 105 is the β1 Subunit of Soluble Guanylate Cyclase as the Heme Proximal Ligand. (1998) *Biochemistry* 37 (13), 4502-9.
Zhao, Y., et al., A Molecular Basis for Nitric Oxide Sensing by Soluble Guanylate Cyclase. (1999) *Proc Nat'l Acad Sci USA* 96 (26), 14753-8.
PCT/US04/03853, PCT International Search Report dated Oct. 28, 2004.

* cited by examiner

*Primary Examiner*—Ralph Gitomer
(74) *Attorney, Agent, or Firm*—Conley Rose, P.C.

(57) ABSTRACT

A method of screening a substance of interest for heme independent modulation of enzymatic activity of soluble guanylyl cyclase (sGC) is disclosed, comprising (a) obtaining $\alpha\beta^{Cys105}$ mutant sGC enzyme; (b) determining activity of the mutant enzyme for forming cGMP from GTP in the presence of the substance of interest in a reaction medium; (c) determining activity as in step (b), except in the absence of the substance of interest; optionally, (d) including an activator other than the substance of interest in steps b) and c); e) comparing results of (b)–(d) to yield a comparison result; and f) from that value of that result, assessing activity of the substance of interest for modulating cGMP production by the mutant enzyme. Increased or decreased formation of cGMP in the presence of the substance of interest indicates activity of the substance for modulating heme independent cGMP production.

6 Claims, 11 Drawing Sheets

SCREENING METHOD FOR IDENTIFYING HEME INDEPENDENT MODULATORS OF SOLUBLE GUANYLYL CYCLASE (SGC) ACTIVITY USING $\alpha\beta^{CYS105}$ MUTANT SGC

CROSS-REFERENCE TO RELATED APPLICATIONS

This application claims the benefit under 35 U.S.C. § 119(e) of U.S. Provisional Patent Application No. 60/446,427 filed Feb. 11, 2003, the disclosure of which is hereby incorporated herein by reference.

STATEMENT REGARDING FEDERALLY SPONSORED RESEARCH OR DEVELOPMENT

Research leading to the present invention was supported in part by the federal government under grants awarded by the National Space Biomedical Research Institute, U.S. Army Medical Research, and the National Institutes of Health. The United States government may have certain rights in the invention.

BACKGROUND OF THE INVENTION

1. Field of the Invention

The invention generally relates to the prevention and treatment of cyclic GMP-dependent pathophysiologies and to the development of drugs for use therein. More particularly, the invention pertains to such prevention, treatment and drug development using methods and compositions that employ a heme-deficient $\alpha\beta^{Cys105}$ mutant soluble guanylyl cyclase (sGC) enzyme or gene.

2. Description of Related Art

Soluble guanylyl cyclase (sGC), is a crucial enzyme in the NO/cGMP dependent pathway. sGC-mediate increase in intracellular cGMP affects smooth muscle relaxation, platelet aggregation, leukocyte adhesion, cell proliferation and migration, neurotransmission and other effects (1). sGC is a heterodimeric protein composed of one α and one β subunit (2). Two isoforms for each subunit (($\alpha_1$, $\alpha_2$, $\beta_1$, $\beta_2$) have been described, with the heterodimer $\alpha_1\beta_1$ ubiquitously expressed. Both subunits are required for a fully active sGC (3). Deletion analysis of the α and β subunits (4) and subsequent site-directed mutagenesis studies delineated some aspects of the domain structure of sGC. The NH2-terminal domains of both subunits play a crucial role in the mediation of the NO-dependent activation of sGC (4). The C-terminal portion of each subunit contains a cyclase homology domain found in all nucleotide cyclases. The C-terminal domains of both subunits are required for the assembly of an active catalytic center (5). The sGC heterodimer contains a heme prosthetic group (6). The heme-containing N-terminal domain, also referred to as the regulatory domain, is separated from the C-terminal catalytic domain by a region believed to be important for the dimerization of sGC (7), although the role of this domain in dimerization remains to be tested. Soluble guanylyl cyclases are often referred to as Nitric Oxide (NO) receptors. NO binds to the heme moiety of sGC (8) and coincide with stimulation of sGC (9), which reaches several hundred-fold with purified enzyme (10–12). Extensive analysis of UV-Vis (11,13), EPR (14) and Raman (15,16) spectra described the transformation of the sGC heme prosthetic group upon binding of nitric oxide. In the absence of NO sGC heme is 5-coordinated with a histidine 105 residue of the β subunit as the axial ligand. Binding of NO to $Fe^{++}$ and formation of nitrosyl heme result in the disruption of the histidine-heme coordinating bond and displacement of iron from the protoporphyrin plane. The kinetic and mechanistic aspects of these transformations are the subject of considerable investigation (17–20). Site-directed mutagenesis studies identified His105 of the β subunit as the axial ligand for the heme moiety (21, 22) and the first 365 residues of the β subunit are sufficient to bind and retain the heme group (23). Although the connection between the formation of the nitrosyl heme and activation of cGMP synthesis is well documented and accepted, little is known about the coupling mechanism between these two events. While the perturbations in the heme moiety of sGC upon NO-binding are well described, the mechanism by which the heme-containing domain regulates sGC catalytic center is not understood. One of the most commonly accepted hypotheses proposes that NO-induced release of the His105 residue allows His105 to exert its function and stimulate the enzyme (24, 25). Toward elucidating the main mechanism of physiological activation and pharmacological inhibition of cGC, there are reports describing the substitution of the heme-coordinating Histidine 105 residue of the bovine β subunit with phenylalanine (21, 40). As this substitution resulted in elimination of NO-dependent regulation of sGC, it proved the crucial role of βHis105 residue in activation of sGC enzyme. To analyze the role of the heme moiety in the activation of sGC by YC-1, the heme-coordinating histidine was substituted with a cysteine residue (26), which is known to coordinate heme in other enzymes, e.g. nitric oxide synthase (43). This report demonstrated that His105 residue is important for the activation of sGC through allosteric activator YC-1, but YC-1-dependent activation can occur without heme, albeit less efficiently.

In summary, it is known that soluble guanylyl cyclase (sGC) is an important enzyme that is involved in the regulation of cardiovascular homeostasis and pathologies (blood pressure, atherosclerosis, septic shock), neurotransmission and sensory perception. This enzyme is the target of a group of compounds known as NO-donors, or such known and widely used drugs as nitroglycerin. Upon activation by these drugs the enzyme synthesizes intracellular messenger cGMP and regulates a number of cellular processes. The enzyme acts as a heterodimer whose activity is regulated by the ferrous heme moiety. The sGC activation methodologies presently in use or in development rely on activation of sGC enzyme by delivering pharmacological compounds (mainly NO donors or allosteric regulators of sGC) or on delivery of NOS genes coding for enzymes that produce NO in order to activate sGC. There is no currently available method that can increase and sustain cGMP levels without drug administration. Another drawback of the methods currently used in practice today is that the effects of nitroglycerin and NO-donors are transient and the patients taking it often develop tolerance to their effects. In addition, some of the allosteric regulators have toxic effects on cellular level.

Inhibition of sGC activity has been shown to be effective in the prevention of septic shock in animals. Conventional inhibitors of sGC are based on the oxidation of the heme moiety of the enzyme. Those inhibitors are not specific since they also affect other heme-containing enzymes. The conventional inhibitors are also not very effective due to the large excess of hemoglobin and myoglobin proteins which buffer the effect of the inhibitors.

BRIEF SUMMARY OF THE PREFERRED EMBODIMENTS

A constitutively active mutation in the regulatory domain of soluble guanylyl cyclase (sGC) mimicking the stimulated state of the enzyme is described. This mutant variant of sGC ($\alpha\beta^{Cys105}$ mutant sGC) employed in the methods described herein does not require exposure to the above-mentioned drugs, or any other drugs, in order to display its catalytic activity. This feature makes it a good candidate for alternative methods to elevate and sustain intracellular cGMP levels. Accordingly, in some embodiments of the present invention, delivery of only the mutant beta ($\beta$) subunit (or beta gene) of the alpha/beta sGC heterodimer is sufficient to affect intracellular cGMP levels, since the mutant beta subunit competes efficiently with the normal beta subunit for sGC assembly.

The preferred methods and compositions take advantage of the fact that this is the first variant of the sGC enzyme that does not require pharmacological activation and is constitutively active. The Histidine 105 residue is known to be important for the binding of the heme moiety of the enzyme. The heme moiety, in turn, is crucial for sGC activation by currently used drugs. Based on similar studies performed with sGC the mutation was expected to abolish sGC activity and make the enzyme insensitive to NO-donors. However, the substitution of His105 by a cysteine residue resulted in an enzyme that does not require activation by NO-donors since it is constitutively activated, even though it lacks the heme moiety and is not responsive to NO. The $\alpha\beta^{Cys105}$ mutant enzyme has the catalytic properties of a normal sGC after administration of drugs. Thus, the constitutively active heme-deficient sGC mutant lacks the flaws of current inhibitors and will find widespread therapeutic uses and as a laboratory tool.

Among other uses, the $\alpha\beta^{Cys105}$ mutant sGC DNA will be useful in gene therapy for the prevention or treatment of a variety of pathophysiologies, and the protein will find use for drug screening. In accordance with certain embodiments of the present invention, a method of screening a substance of interest for heme independent inhibition of soluble guanylyl cyclase is provided. The method comprises a) obtaining purified $\alpha\beta^{Cys105}$ mutant soluble guanylyl cyclase enzyme or a cell lysate containing $\alpha\beta^{Cys105}$ mutant soluble guanylyl cyclase enzyme; b) assaying the purified enzyme or cell lysate for formation of cGMP from GTP in the presence of the substance; and c) assaying the purified enzyme or cell lysate for formation of cGMP from GTP in the absence of the substance. In some embodiments, the method also includes: d) carrying out steps b) and c) in the presence or absence of an activator. The results from steps b), c), and d), if present, are compared to determine whether the substance inhibits cGMP production by the purified enzyme or cell lysate.

In accordance with another embodiment of the present invention, a method of screening a substance of interest for heme independent activation of soluble guanylyl cyclase is provided. This method comprises a) obtaining purified $\alpha\beta^{Cys105}$ mutant soluble guanylyl cyclase enzyme or a cell lysate containing $\alpha\beta^{Cys105}$ mutant soluble guanylyl cyclase enzyme; b) assaying the purified enzyme or cell lysate for formation of cGMP from GTP in the presence of the substance; and c) assaying the purified enzyme or cell lysate for formation of cGMP from GTP in the absence of the substance. In some embodiments, this method also includes: d) carrying out steps b) and c) in the presence or absence of an activator other than the substance of interest. The results from steps b), c), and, d), if present, are compared to determine whether the substance enhances cGMP production by the purified enzyme or cell lysate.

Also provided by the present invention is a method to identify, or aid in identifying, a functional region of soluble guanylyl cyclase that is responsible for sGC regulation. The method includes a) obtaining a library of deletion mutants of $\alpha$ subunit of soluble guanylyl cyclase; b) producing mutant sGC enzymes containing $\beta^{Cys105}$ subunit and $\alpha$ subunits with deletions obtained in step a); and c) obtaining cell lysates comprising the respective mutant sGC enzymes with $\alpha$ subunit deletions, from step b). In certain embodiments, the method includes: d) purifying the mutant sGC enzymes from step c). The method further comprises: e) assaying the purified enzymes or cell lysates from step c) or d) for formation of cGMP from GTP in the absence of activators or inhibitors; f) assaying purified wild type sGC enzyme, or a cell lysate comprising the wild type sGC enzyme, for formation of cGMP from GTP in the absence of activators or inhibitors; and g) assaying purified $\alpha\beta^{Cys105}$ mutant sGC enzyme, or a cell lysate comprising the $\alpha\beta^{Cys105}$ sGC enzyme, for formation of cGMP from GTP in the absence of activators or inhibitors. The results from e), f) and g) are compared to determine whether any of the $\alpha$ subunit deletions decreases or increases the activity of the corresponding mutant enzyme tested in step e), as compared to the $\alpha\beta^{Cys105}$ mutant sGC enzyme in step g), to levels comparable or identical to that of the wild type sGC enzyme in step f). Using those results, an $\alpha$ subunit deletion mutant from step a) is identified which contains a critical or non-critical region that effects sGC activation. An effector region of the sGC protein may have a modulating function on the sGC enzymatic activity (e.g., effecting a transducing signal), or it may be important or critical for enzyme activation or function (e.g., all or part of the active site of the enzyme).

In accordance with certain embodiments of the present invention, a method to aid in identifying functional regions or structural features of soluble guanylyl cyclase stimulation is provided. In some embodiments the purified $\alpha\beta^{Cys105}$ mutant soluble guanylyl cyclase enzyme is crystallized in the presence of DTT and/or in the absence of DTT. The resulting soluble guanylyl cyclase enzyme crystals are then compared and structural changes in the soluble guanylyl cyclase protein associated with the presence or absence of DTT are determined.

Some embodiments of the present invention provide a method of increasing and/or sustaining intracellular production of cyclic GMP in a mammalian cell which include: providing $\alpha\beta^{Cys105}$ mutant soluble guanylyl cyclase, or the $\beta^{Cys105}$ subunit thereof, to the cell in vitro or in vivo. In certain embodiments, the method additionally or alternatively includes constitutively expressing in the cell the $\alpha\beta^{Cys105}$ mutant soluble guanylyl cyclase gene, or a portion thereof containing at least the DNA coding for the $\beta^{Cys105}$ subunit.

Also provided in accordance with certain embodiments of the present invention are methods of treating, attenuating or preventing a mammalian pathophysiologic condition associated with cyclic GMP regulation of a cellular process. In some embodiments, the method includes increasing and/or sustaining cGMP production by delivering the $\alpha\beta^{Cys105}$ mutant soluble guanylyl cyclase enzyme, or the $\beta^{Cys105}$ subunit thereof, to at least one cell in vivo. In some embodiments, increasing and/or sustaining cGMP production comprises delivering the $\alpha\beta^{Cys105}$ mutant soluble guanylyl cyclase gene, or the $\beta^{Cys105}$ subunit portion thereof, to at least one cell in the mammal. Because the effects of conventional drugs such as nitroglycerin and NO-donors are typically transient, and the recipients often develop tolerance to the drugs' effects, the use of intrinsically active $\alpha\beta^{Cys105}$ mutant sGC eliminates the need for activation and is also expected to abolish the problem of tolerance.

In some embodiments, the treatment, attenuation or prevention of a mammalian pathophysiologic condition associated with cyclic GMP regulation of a cellular process comprises inhibiting cGMP production by administering an inhibitor of soluble guanylyl cyclase that acts independently of the heme moiety of soluble guanylyl cyclase, in a mammal in need of such treatment, attenuation or prevention.

In certain embodiments the method of treating or preventing a mammalian pathophysiologic condition associated with cGMP regulation of a cellular process comprises treating or attenuating angina. In some embodiments the pathophysiologic condition comprises a cardiovascular disease, including, but not limited to, chronic heart disease, chronic hypertension, thrombosis, atherosclerosis, congestive heart failure and myocardial infarction. In some embodiments the pathophysiologic condition comprises a post-angioplasty complication or a complication arising from a vein graft operation. In other embodiments the method of treating or preventing a pathophysiologic condition associated with cGMP regulation of a cellular process includes treating a tumor or attenuating or preventing tumor metastasis. In still other embodiments, the method of treating or preventing a mammalian pathophysiologic condition associated with cGMP regulation of a cellular process comprises treating or attenuating a penile dysfunction. In yet another embodiment the pathophysiologic condition comprises septic shock. Still other embodiments, advantages and features of the present invention will be apparent from the description and drawings which follow.

DETAILED DESCRIPTION OF PREFERRED EMBODIMENTS

Figure 1A:
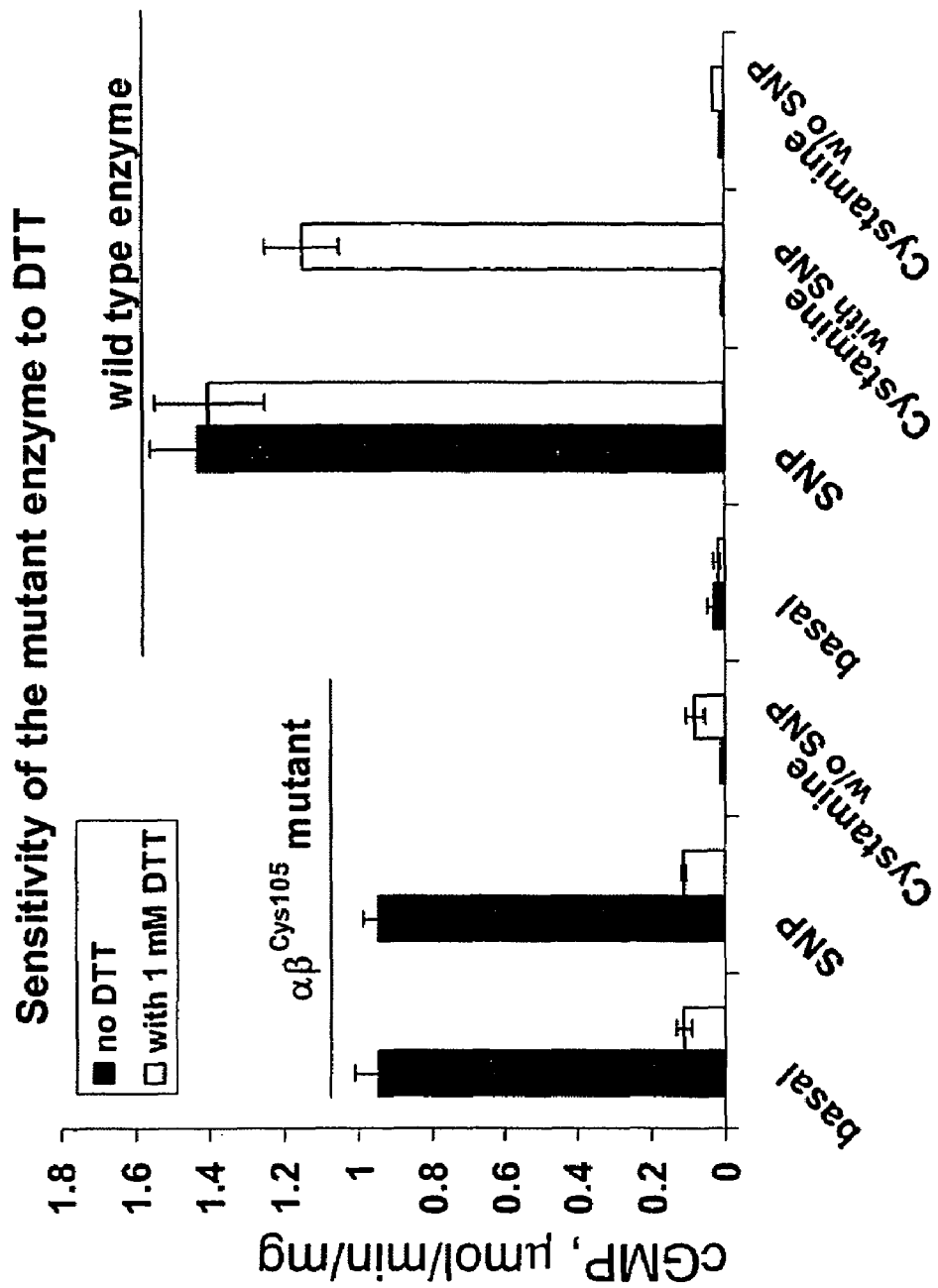
FIGS. 1A–B are graphs showing that the mutant $\alpha\beta^{Cys105}$ enzyme has a high activity inhibited by DTT (FIG. 1A), but not GSH (FIG. 1B).

A heme-deficient mutant sGC with a substituted Hist105 residue is described herein, which has a high basal specific activity and displays properties similar to NO-stimulated wild type sGC. The role of the heme-coordinating bond and of the coordinating His105 residue in governing the function of the sGC regulatory domain is discussed. The heme-coordinating His105 residue of the β subunit of soluble guanylyl cyclase was substituted with cysteine, resulting in a heme-deficient enzyme. Analysis of this enzyme indicated that the mutant sGC has a high basal activity comparable with the activity of the wild type sGC activated by nitric oxide. The mutant was significantly inhibited by DTT, but not glutathione, and was heme-insensitive without DTT. The mutant can be partially reconstituted with heme after treatment with DTT and is activated by NO, although both heme and NO activation are lost after gel filtration. The mutant is only partially stimulated by NO-independent activators such as protoporphyrin IX, fatty acids and allosteric activators, but the DTT-inhibited mutant shows activation by these reagents. Intracellular mutant sGC displays a remarkably high level of cGMP synthesis, which is also not affected by nitric oxide. Based on the properties of this constitutively active $\alpha\beta^{Cys105}$ enzyme a revision of the functional role of the His105 residue is proposed. The mechanism of sGC activation by NO is discussed.

Materials and Methods

Reagents. Hemin, Grace media, FBS and imidazole were purchased from Sigma. The NO donor 3-(2-hydroxyl-1-methyl-2nitrosohydrazino)-N-methyl-1-propanamine (NOC-7) was from Calbiochem. The 3-(5'-Hydroxymethyl-2'furyl)-1-benzyl-indazole (YC-1) activator was from Alexis Co. [$\alpha^{32}$P] GTP was from NEN.

cDNA's and Expression Vectors. The design and generation of baculoviruses expressing sGC α and β subunits and the generation of the site-directed substitution of βHis105 were described previously (26) (appended hereto).

sGC Expression and Purification. Wild type and $\alpha\beta^{Cys105}$ mutant sGC were expressed in Sf9 cells as described previously (26). Purification of sGC was performed as described earlier (26), the disclosure of which is hereby incorporated herein by reference, with the following modifications. Cells were harvested 72 h post infection, resuspended in loading buffer (25 mM triethanolamine, pH 7.5. 10 glycerol, 4 mM $MgCl_2$ and 1 mM phenylmethylsulfonyl fluoride, and 5 µg/ml each of pepstatin A, leupeptin, aprotinin, and chymostatin,) and lysed by sonication. The lysate was subjected to 100,000×g centrifugation for 1 h. The high-speed supernate was loaded on a 60 ml DEAE-Sepharose (Amersham Pharmacia Biotech) column and washed with 60 ml of loading buffer without protease inhibitors. The proteins were eluted with loading buffer containing 250 mM NaCl and the eluate was directly loaded on a 30 ml His-Bind resin (Novagen) column. The column was washed with 60 ml of loading buffer followed by 60 ml of loading buffer with 45 mM imidazole. The enzyme was eluted with 175 mM imidazole and 2 ml fractions were collected. The absorbance spectra (wild type enzyme) and activity (both wild type and $\alpha\beta^{Cys105}$ mutant) in the elution fractions were determined and the positive fractions were pooled for further studies. The enzyme at this stage was approximately 90–95% pure. To remove imidazole, sGC-containing fractions were diluted 3 fold with 25 mM triethanolamine pH 7.5, loaded on a 2 ml Hi-Trap DEAE- Sepharose column (Amersham Pharmacia Biotech), washed with 10 ml of loading buffer and eluted with 25 mM triethanolamine pH 7.5, 250 mM NaCl, 10 glycerol, 4 mM $MgCl_2$, 0.5 mM EDTA, 0.5 mM EGTA. The enzyme obtained at this stage (95% or greater purity) was used for experiments.

Assay of sGC Activity. Enzyme activity was assayed by formation of [$^{32}$P] cGMP from $\alpha$[$^{32}$P]GTP at 37° C. in a final volume of 100 µl. Incubation medium contained 50 mM triethanolamine-HCl buffer (pH 7.4), 1 mM 3-isobutyl-1-methylxanthine (IBMX), 1 mg/ml BSA. 1 mM cGMP, 3 mM $MgCl_2$, 0.05 mg/ml creatine phosphokinase, 5 mM creatine phosphate, 0.1 mM EGTA. 200 µM GTP (about 10.000 cpm/pmol). The reaction was started by addition of the substrate (GTP) with or without activators. 1 mM DTT, GSH or cysteine were added to the incubation medium before the addition of GTP. Thiol concentration varied in some experiments as indicated. Samples containing 0.2 µg sGC were incubated for 10 or 15 min and the reaction was stopped by addition of 500 µl 150 mM zinc acetate and 500 µl 180 mM sodium carbonate. The pellet of zinc carbonate containing most of the unreacted GTP was removed by centrifugation and the supernatant fractions were loaded onto columns filled with 1 g of neutral alumina. Columns were then eluted with 10 ml 0.1 M Tris-HCl buffer (pH 7.5) and Cherenkov radiation in flow through plus eluate was counted in a LKB liquid scintillation spectrometer. Samples incubated in the absence of sGC were used as a negative control. The concentration of dimethylsulfoxide (DMSO) used as a vehicle for YC-1 was not higher than 0.1 and had no effect on sGC activity as determined previously.

UV-Vis Spectroscopy. All absorbance measurements were recorded with a dual-beam Cecil 9500 spectrophotometer at 25° C. To monitor the heme reconstitution of the $\alpha\beta^{Cys105}$ mutant, 2 µM $\alpha\beta^{Cys105}$ sGC in 25 mM triethanolamine pH 7.5, 10% glycerol, 250 mM NaCl, 4 mM $MgCl_2$, 0.5 mM EDTA and 0.5 mM EGTA were treated with 2 mM DTT for 15 min at room temperature. Hemin stock solution (5 mM) was prepared in DMSO and was reduced by dilution in 25 mM TEA, pH 7.5 containing 5 mM DTT to a working solution of 500 µM. The reduced heme was kept under argon in a gas-tight vial during the reconstitution. Identical amounts of reduced hemin (between 0.1 µM to 15 µM were added with a gas-tight syringe to both sample and reference cuvettes, which contained 25 mM triethanolamine pH 7.5, 10% glycerol, 250 mM NaCl, 4 mM $MgCl_2$, 0.5 mM EDTA, 0.5 mM EGTA and 2 mM DTT. Difference spectra were recorded between 370 and 600 nm with a speed of 200 nm/min. To measure the effects of NO on the spectra of reconstituted $\alpha\beta^{Cys105}$ enzyme, 50 µM NOC-7 was added to both sample and reference cuvettes and spectra recorded 15 min later.

Assay of cGMP Accumulation in Intact Cells. 48 hours postinfection SF9 cells expressing either wild type or $\alpha\beta^{Cys105}$ mutant sGC were washed twice with Dulbecco's PBS and preincubated for 10 min in PBS with 0.5 mM IBMX in 50 µl final volume of 107 cell/ml cell suspension. After this, 1 mM SNP or vehicle was added and the cells are incubated for an additional 5 min at 37° C. The reaction was terminated by addition of 50 µl of 1 M perchloric acid and cGMP was extracted on ice for 1 h. The extract was centrifuged, neutralized with 2M $K_2CO_3$ and used for cGMP determination by radioimmunoassay (9, 27). The pellet was dissolved in 0.1 M NaOH and used for protein assay by the method of Lowry (28).

SDS-PAGE and Western Blot. Purified sGC was separated on 7.5 SDS-PAGE as described previously (29) and transferred to Immobilon™-P membrane (Millipore Corp. Bedford, Mass.) according to manufacturer's protocol. Immunodetection of non-tagged (3 subunit was performed using a 1:1000 dilution of polyclonal rabbit antibodies raised against β subunit of human sGC (12). Hexahistidine-tagged a subunit was detected by using 1:2000 dilution of monoclonal anti-hexahistidine antibodies (Quiagen). Blots were developed using the ECL detection system (Amersham Pharmacia Biotech) according to the manufacturer's protocol. Coomassie Blue R250 staining of SDS-PAGE gels was performed as described previously (29).

EXAMPLE 1

DTT Effects on Mutant Enzyme and Wild Type Enzyme

Sensitivity of the mutant $\alpha\beta^{Cys105}$ enzyme to DTT was determined, and the results are shown in FIG. 1A, together with results for the wild type enzyme. The activity of purified $\alpha\beta^{Cys105}$ or wild type enzymes was measured with 1 mM DTT (open bars) or in the absence of any thiols (solid bars). The activity of enzyme was measured with 100 µM SNP or without SNP (basal) as described in Materials and Methods To test the effects of Cystamine on sGC, the enzyme was first preincubated for 5 min at room temperature with 1 mM Cystamine in the presence or absence of 1 mM DTT and then the activity was measured in the presence of 1 mM Cystamine. Referring now to the graph shown in FIG. 1B, the effects of DTT and GSH on the $\alpha\beta^{Cys105}$ were compared. Purified $\alpha\beta^{Cys105}$ mutant enzyme was preincubated with reaction buffer (see Material and Methods) containing indicated concentrations of GSH (opened squares, dotted line) or DTT (solid diamonds, solid line) for 10 min at room temperature and then tested for activity. One sample (opened triangle) was treated with 10 mM GSH, then supplemented with 1 mM DTT before the activity was tested. The data are normalized to the sample without any thiols (specific activity 1±0.1 pmol/min/mg) which is defined as 100. Arrow indicates the decrease in activity after the addition of DTT to GSH-treated enzyme. Data representative of 5 independent experiments with similar results performed in triplicates are shown. Values are shown as means±s.d. The results of these tests, demonstrating that the mutant $\alpha\beta^{Cys105}$ enzyme has a high activity inhibited by DTT, but not GSH, are discussed in the Results, below.

EXAMPLE 2

YC-1 Stimulation with/without DTT

Figures 2A, 2B:
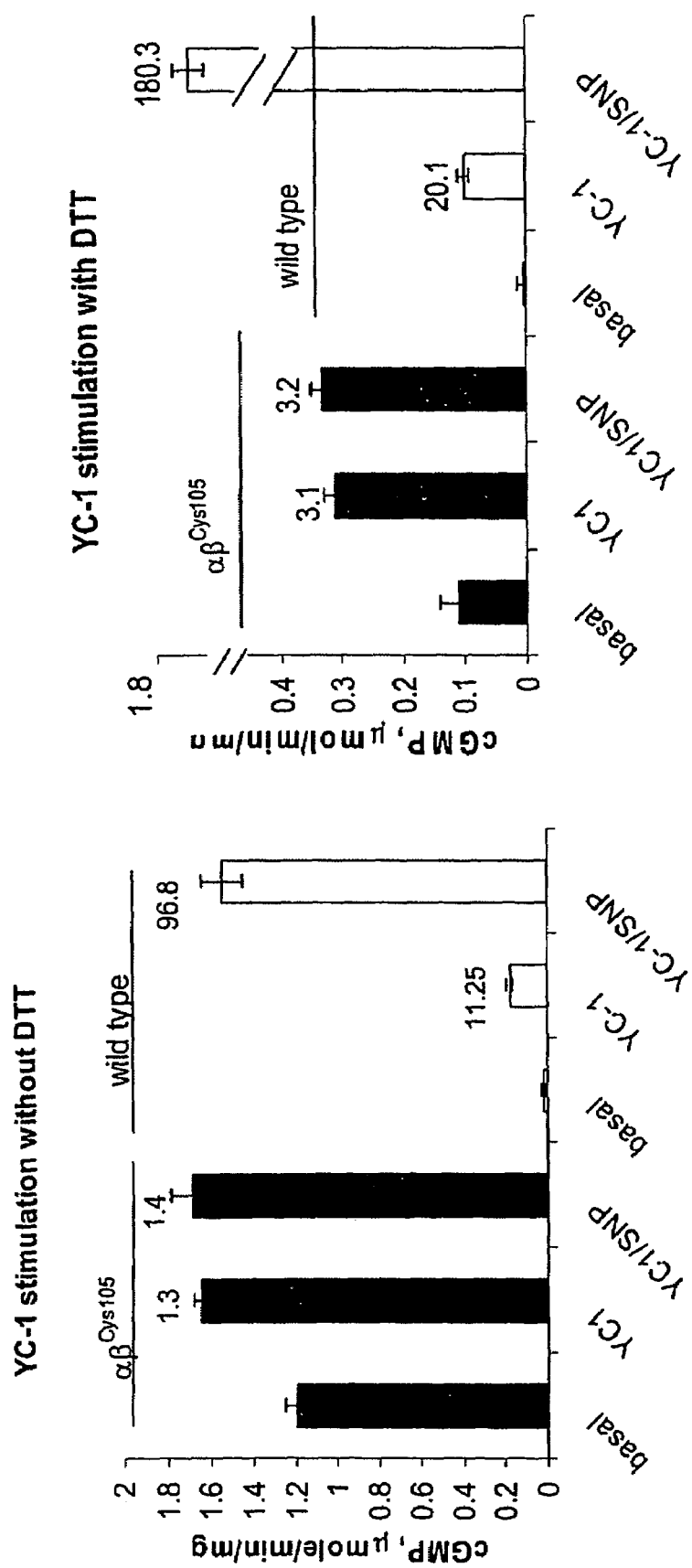
FIGS. 2A–B are bar graphs showing that the allosteric activator YC-1 activates the $\alpha\beta^{Cys105}$ mutant more effectively in the presence of DTT (FIG. 2B) than without (FIG. 2A).

Studies were carried out to determine the effects of the allosteric activator YC-1, and the results are shown in FIGS. 2A–B. The activity of $\alpha\beta^{Cys105}$ (solid bars) and wild type enzyme (opened bars) preincubated with (B) or without (A) 1 mM DTT was tested in the presence of vehicle (DMSO), 100 µM YC-1, 100 µM SNP, or both YC-1 and SNP as described in Material and Methods. The numbers above bars indicate the fold stimulation versus vehicle-treated enzyme. Data representative of 3 independent experiments with similar results performed in triplicates are shown. Values are shown as means±s.d. The experimental data shows that YC-1 activates the $\alpha\beta^{Cys105}$ mutant more effectively in the presence of DTT (FIG. 2B) than without (FIG. 2A), also discussed below in the Results.

EXAMPLE 3

Effect of Arachidonic Acid on Mutant Enzyme Activity

Figure 3:
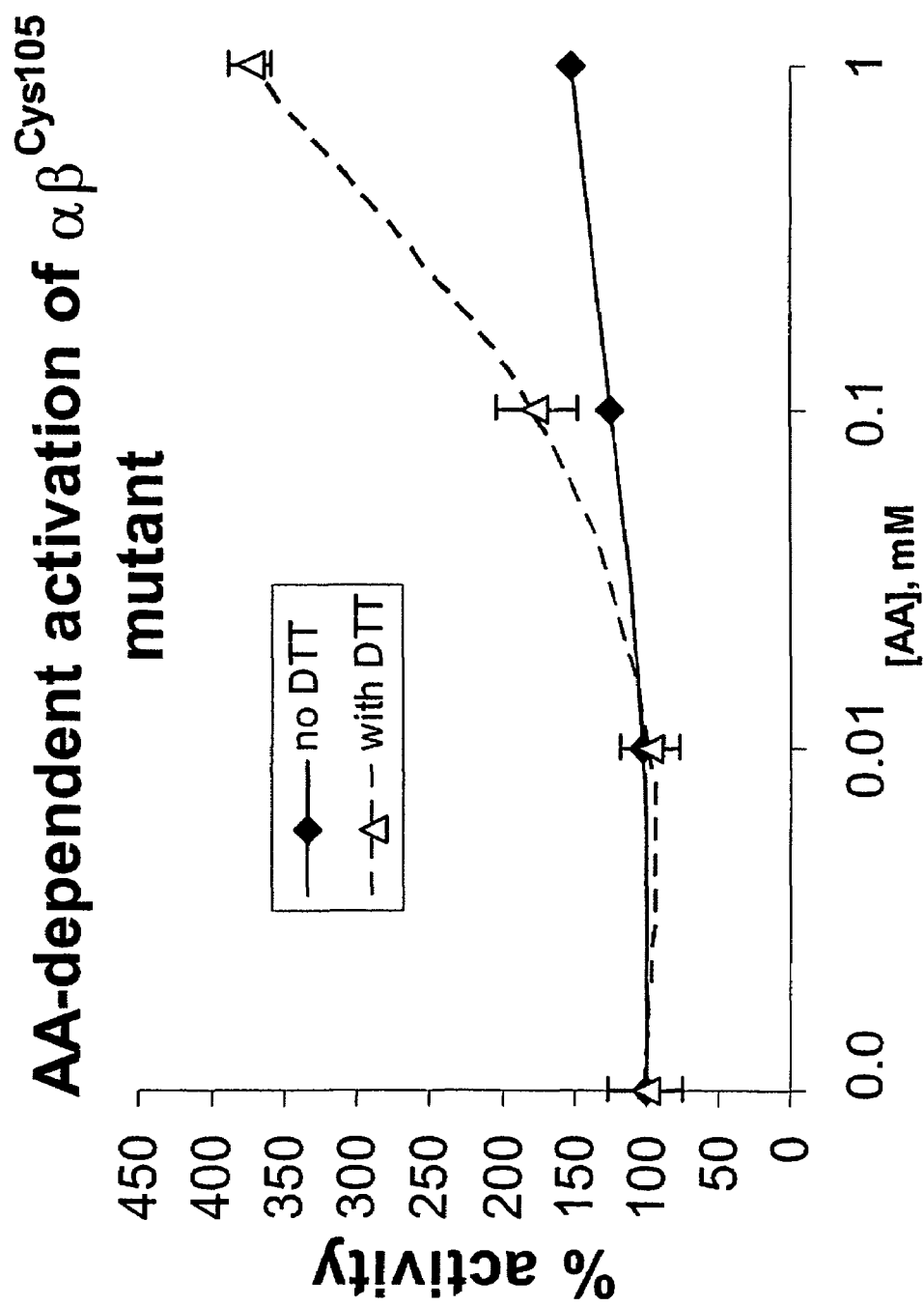
FIG. 3 is a graph showing arachidonic acid (AA) dependent activation of $\alpha\beta^{Cys105}$ mutant enzyme over a range of AA concentrations.

The activity of the purified $\alpha\beta^{Cys105}$ enzyme was measured in the presence of increasing concentrations of AA with (opened triangles, dotted line) or without (solid diamonds, solid line) 1 mM DTT. The data in each treatment group are normalized to sample without AA, which is defined as 100. Data representative of 3 independent experiments with similar results performed in triplicates are shown in FIG. 3. Values are shown as means±s.d. Specific activity of the DTT-treated enzyme without AA in this experiment was 0.13±0.03 µmol/min/mg, and the specific activity of non-treated enzyme was 1.14±0.05 µmol/min/mg. These results, which are discussed below, reveal that AA activates $\alpha\beta^{Cys105}$ mutant sGC more effectively in the presence of DTT than in its absence.

EXAMPLE 4

PPIX Activation of Wild Type and Mutant sGC

Figure 4:
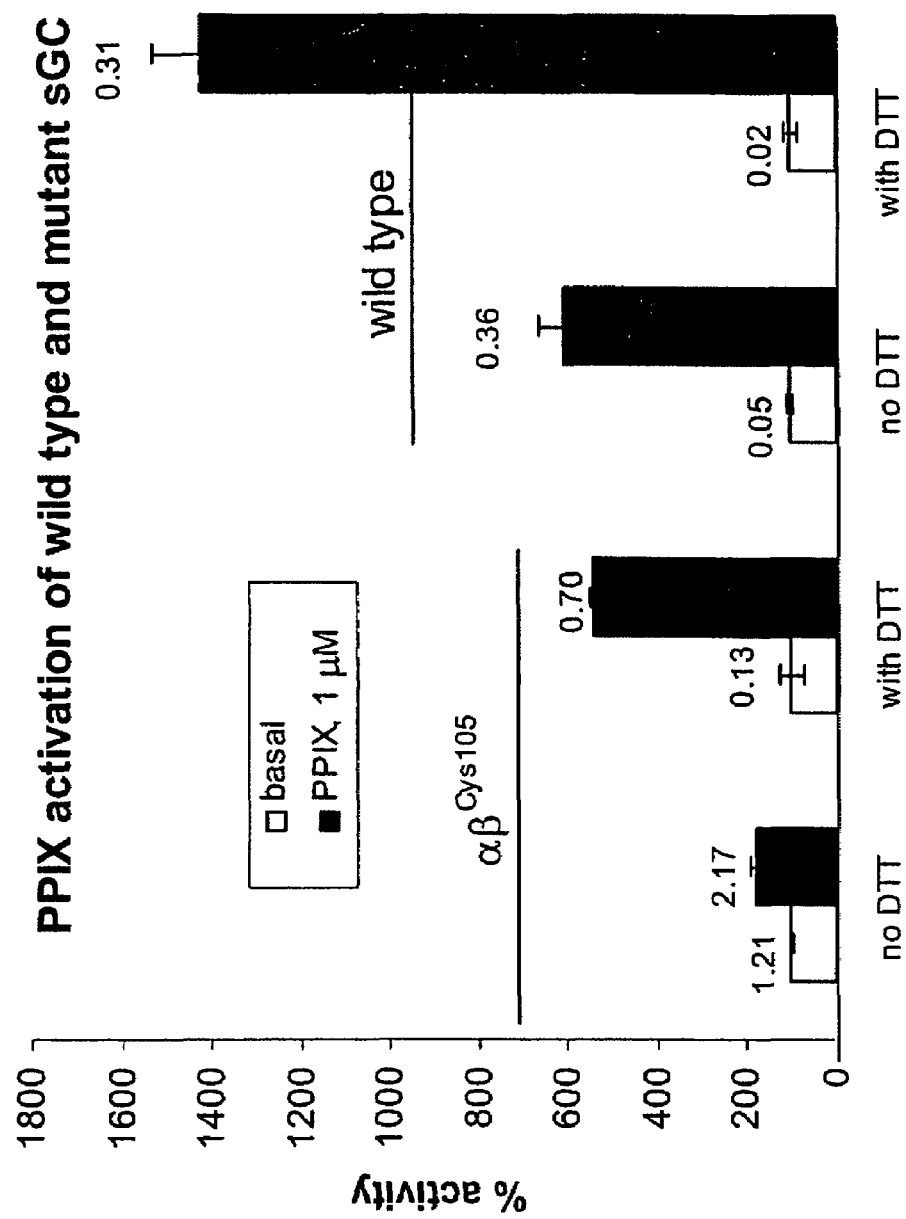
FIG. 4 is a bar graph showing PPIX-dependent activation of wild type and $\alpha\beta^{Cys105}$ mutant enzymes.

The activity of the purified $\alpha\beta^{Cys105}$ enzyme was measured in the absence (opened bars) or presence of (solid bars) 1 µM protoporphyrin. Before addition of PPIX the enzymes were treated with 1 mM DTT or treated with vehicle. The data in each treatment pair are normalized to sample without PPIX assumed as 100. The numbers above bars indicate the specific activity of the sample in µmol/min/mg. Data representative of 3 independent experiments with similar results performed in triplicates are shown in FIG. 4. Values are shown as means±s.d. PPIX-dependent activation of wild type and $\alpha\beta^{Cys105}$ mutant enzymes is discussed below in Results.

EXAMPLE 5

Heme Reconstitution of $\alpha\beta^{Cys105}$ Enzyme and SNP or YC-1 Stimulation

Activation by 100 µM YC-1 and/or 100 µM SNP was tested on a DTT-treated heme reconstituted $\alpha\beta^{Cys105}$ enzyme. SNP stimulation: Mutant $\alpha\beta^{Cys105}$ enzyme was incubated with (FIG. 5A, open bars) or without (FIG. 5A, solid bars) 1 mM DTT for 15 min at room temperature and reconstituted with 1 µM hemin reduced as described in Materials and Methods. The activity of the reconstituted enzyme was tested in the presence or absence of 100 µM SNP. One sample was reconstituted with 10 µM hemin, then subjected to gel filtration through a Hitrap Desalting column (Amersham Pharmacia Biotech) and activity was tested in the presence of 100 µM SNP (after GF).

Figure 5A:
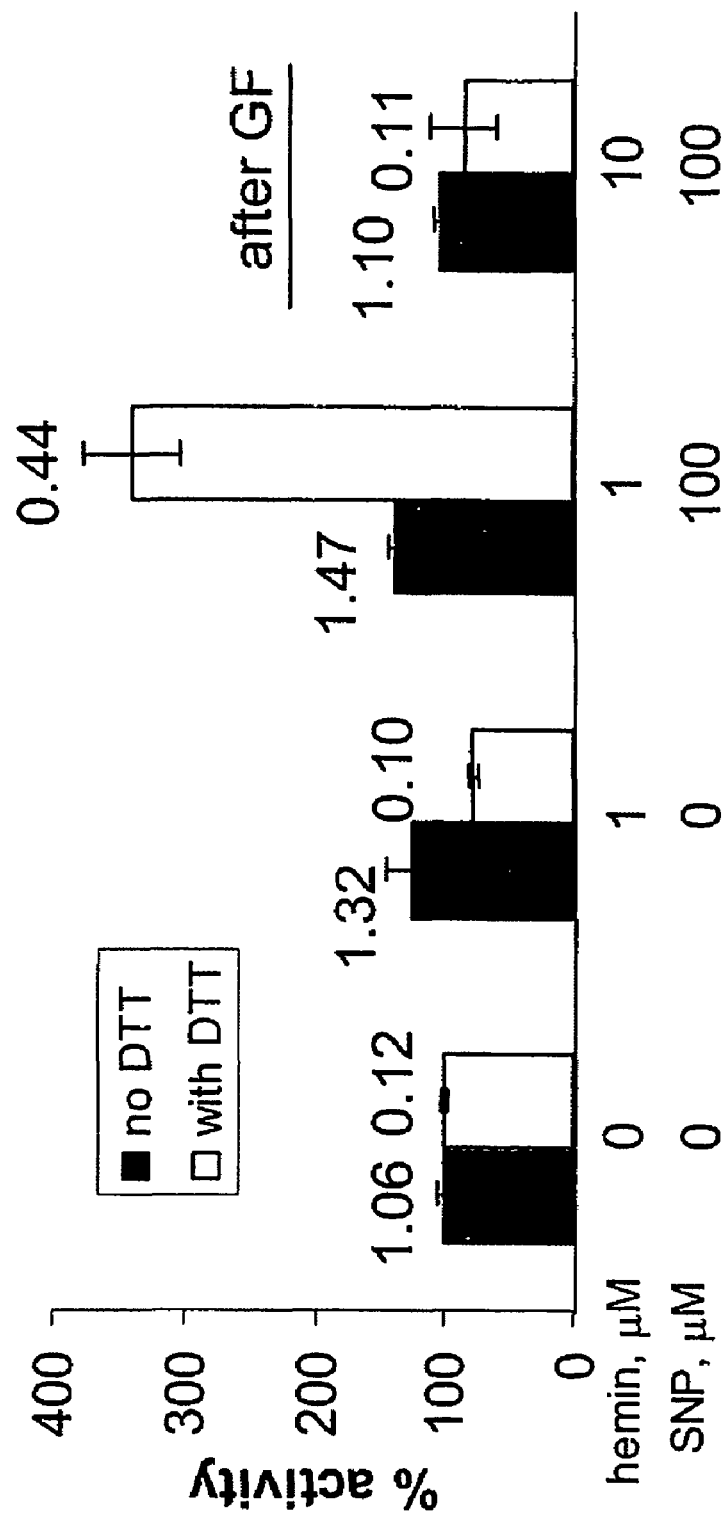
FIGS. 5A–D are graphs showing heme reconstitution and SNP (FIG. 5A) or YC-1 (FIG. 5B) stimulation, and spectral data for the mutant enzyme with/without hemin (FIGS. 5C/D).
Figure 5B:
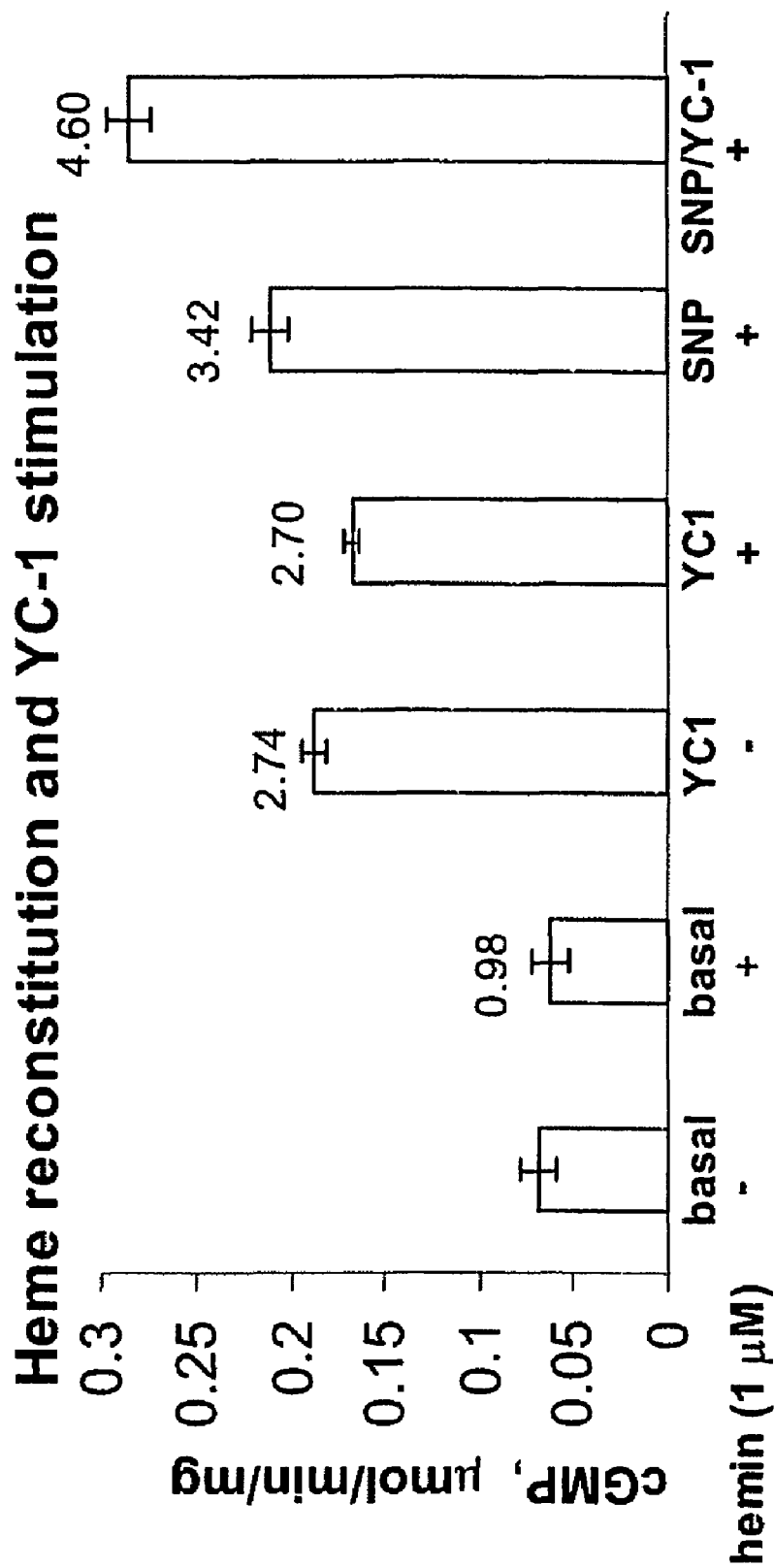

Allosteric activation: The numbers above bars indicate the specific activity (FIG. 5A pmole/mg/min) or fold stimulation versus the basal activity of heme-deficient $\alpha\beta^{Cys105}$ enzyme (FIG. 5B). Data representative of 4 (FIG. 5A) or 3 (FIG. 5B) independent experiments with similar results performed in triplicates are shown. Values are shown as means±s.d.

Figures 5C, 5D:
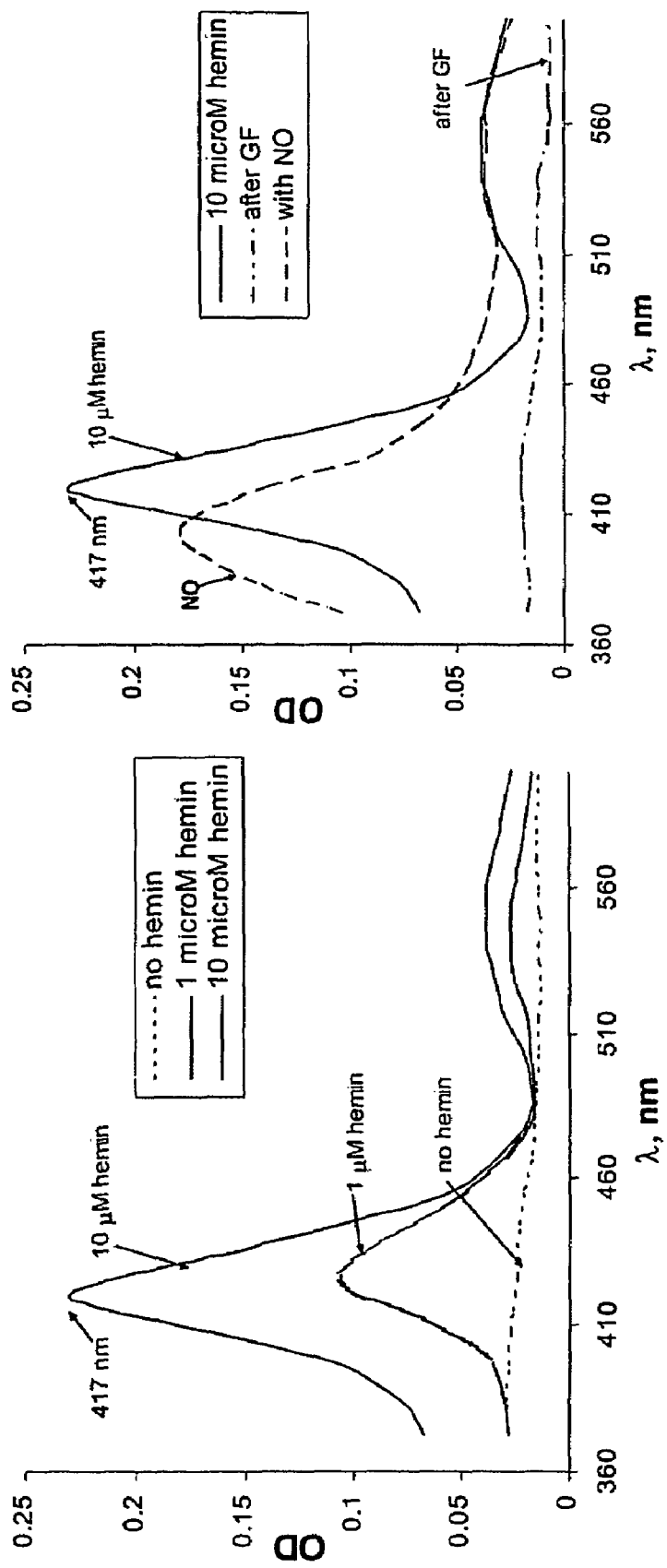

Absorption spectra of reconstituted enzyme are shown in FIGS. 5C,D. Difference spectra of 2 µM heme-deficient DTT-treated $\alpha\beta^{Cys105}$ enzyme (no hemin) and enzyme reconstituted with increasing concentrations of reduced hemin was recorded as described in Materials and Methods. Spectra of $\alpha\beta^{Cys105}$ enzyme without hemin or reconstituted with 1 µM and 10 µM hemin are shown in FIG. 5C. The enzyme reconstituted with 10 µM hemin was subjected to gel filtration (after GF) or treated for 15 min with 50 µM NOC-7 (with NO) and the spectra recorded, as shown in FIG. 5D.

EXAMPLE 6

Figures 6A, 6B:
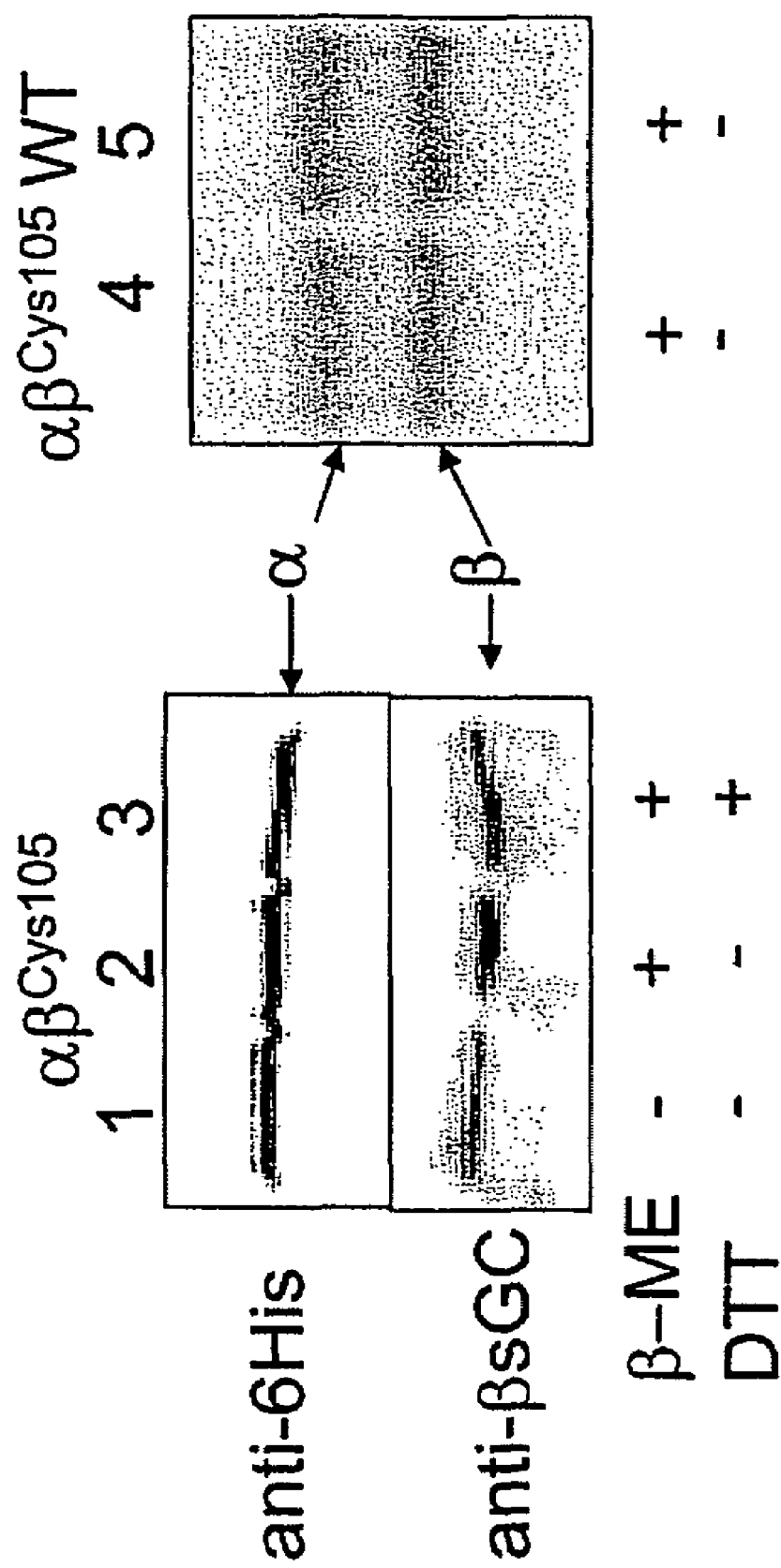
FIGS. 6A–B depict Western blotted (FIG. 6A) and Coomassie stained (FIG. 6B) SDS-PAGEs showing that no disulfide bonds between mutant sGC subunits are formed.

Purified mutant $\alpha\beta^{Cys105}$ enzyme (5 µg) was incubated with 2 mM DTT for 1 hour at room temperature or treated directly with non-reducing (−β-ME, lane 1) or reducing (+β-ME, lanes 2 and 3) loading SDS-PAGE buffer. Western blotting with anti-6His and anti-β-sGC antibodies was performed to determine the position of hexahistidine-tagged α (FIG. 6A, top panel) and β subunits (FIG. 6A, bottom panel), respectively. In a separate experiment the mobility of the α and β subunits of $\alpha\beta^{Cys105}$ mutant (FIG. 6B, lane 4) and wild type enzymes (FIG. 6B, lane 5) was visualized by Coomassie staining of 5 µg purified sGC separated by SDS-PAGE. As discussed in Results, below, these data show that no disulfide bonds between mutant sGC subunits are formed.

EXAMPLE 7

Intracellular Accumulation of cGMP in Sf9 Cells

Figure 7:
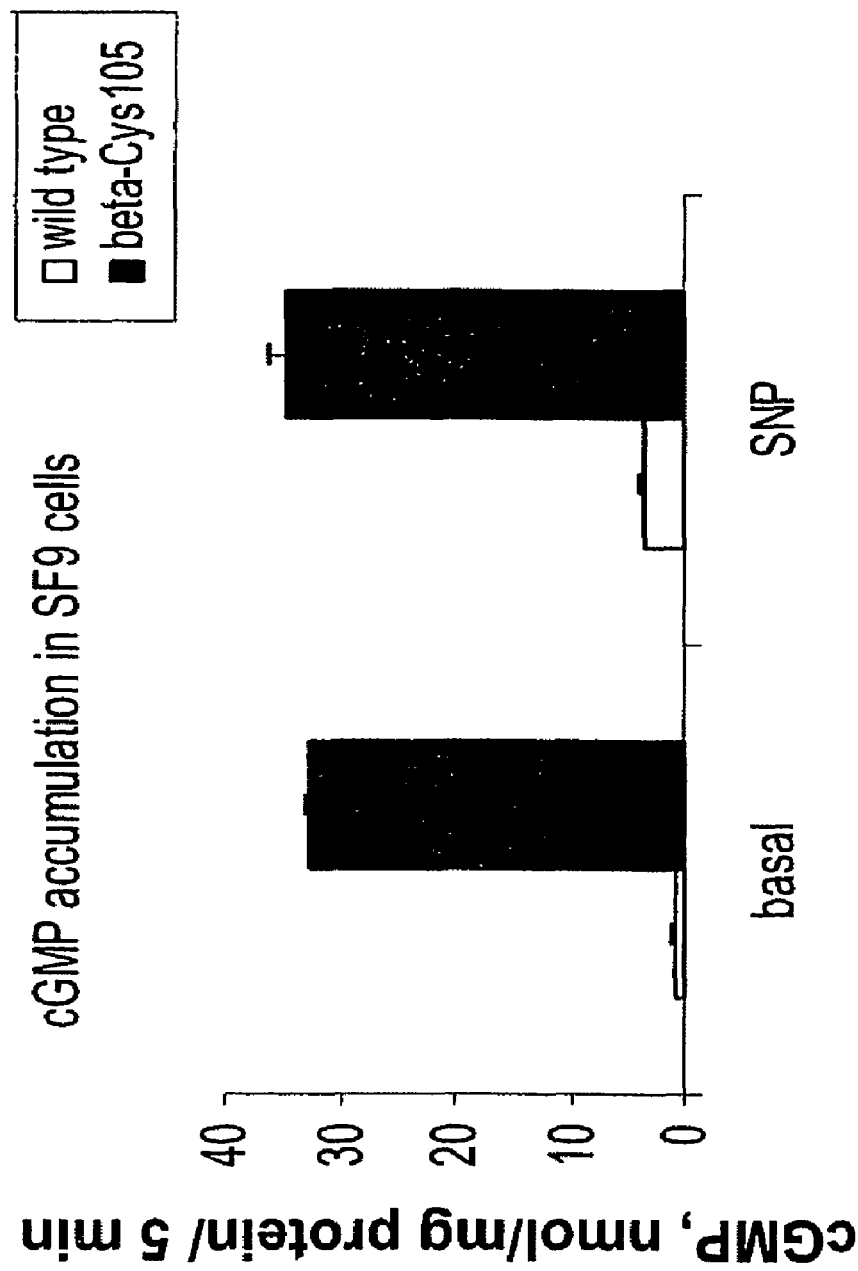
FIG. 7. is a bar graph comparing intracellular accumulation of cGMP in Sf9 cells expressing wild type sGC or $\alpha\beta^{Cys105}$.

Sf9 cells expressing wild type SGC (FIG. 7, open bars) or $\alpha\beta^{Cys105}$ sGC (FIG. 7, solid bars) were harvested, washed with PBS, and challenged with vehicle or 1 mM SNP for 5 min in the presence of 0.5 mM IBMX. Accumulated cGMP was extracted and quantified as described in Materials and Methods. Data representative of 3 independent experiments with similar results performed in sextuplicates are shown in FIG. 7. Values are shown as means±s.d. The differences in intracellular accumulation of cGMP in Sf9 cells expressing the wild type enzyme or the mutant form are discussed below.

Results

Heme Deficient $\alpha\beta^{Cys105}$ Mutant sGC has Different Specific Activity in the Presence or Absence of DTT.

Baculoviruses expressing the sGC α subunit with a C-terminal histidine tag and the β subunit carrying a His105→Cys substitution were used to generate the mutant $\alpha\beta^{Cys105}$ enzyme as described previously (26). The enzyme was heme deficient and did not respond to nitric oxide stimulation (FIG. 1A), which corroborates previous findings (26). Typically, sGC activity in vitro is measured in the presence of at least 1 mM DTT. Specific activity of the $\alpha\beta^{Cys105}$ enzyme in the presence of 1 mM DTT was 0.15 µmol/min/mg. with or without addition of sodium nitroprusside (FIG. 1, white bars). Under similar conditions the wild type enzyme had a specific activity of 0.02 µmol/min/mg without NO and 1.4 µmol/min/mg in the presence of sodium nitroprusside (SNP). These values are in agreement with previous measurements (26). However, when the activity was measured in the absence of DTT, we observed a significant change in the catalytic properties of the $\alpha\beta^{Cys105}$ mutant. While the activity of the wild type enzyme did not change significantly without DTT (FIG. 1, compare white and black bars), the mutant $\alpha\beta^{Cys105}$ enzyme showed a significantly higher activity (0.95 µmol/min/mg, FIG. 1, compare white and black bars) even in the absence of any sGC activators. The addition of SNP did not change the activity of the $\alpha\beta^{Cys105}$ mutant, but significantly increased the activity of the wild type enzyme (FIG. 1A).

To test whether the mutation affected the properties of the catalytic center of sGC the Km for $Mg^{++}$-GTP substrate was measured. We found that the GTP-Km for the $\alpha\beta^{Cys105}$ mutant was about 150 μM both in the presence or absence of DTT (Table 1). These values are well within the 65–450 μM range of GTP-Km measured for the recombinant sGC (12, 30–32), suggesting that the mutation did not affect the catalytic center. Treatment of wild type sGC with thiol modifying agents including cystamine and cystine (33, 34) have been shown to inhibit sGC, presumably by modification of some thiol groups essential for catalysis. We compared the inhibitory effect of cystamine on the $\alpha\beta^{Cys105}$ mutant and wild type enzymes (FIG. 1A). In corroboration with previous reports (33), wild type sGC was inhibited by cystamine and this inhibition was reversed in the presence of DTT. The mutant $\alpha\beta^{Cys105}$ enzyme exhibited a similar sensitivity to cystamine, but was less sensitive in the presence of DTT, supporting the conclusion that the catalytic sites of the wild type and $\alpha\beta^{Cys105}$ enzymes have similar properties. Thus, the His105→Cys substitution significantly increased the activity of the $\alpha\beta^{Cys105}$ mutant not through changes in the catalytic center, but rather by affecting the mechanism of sGC regulation.

Figure 1B:
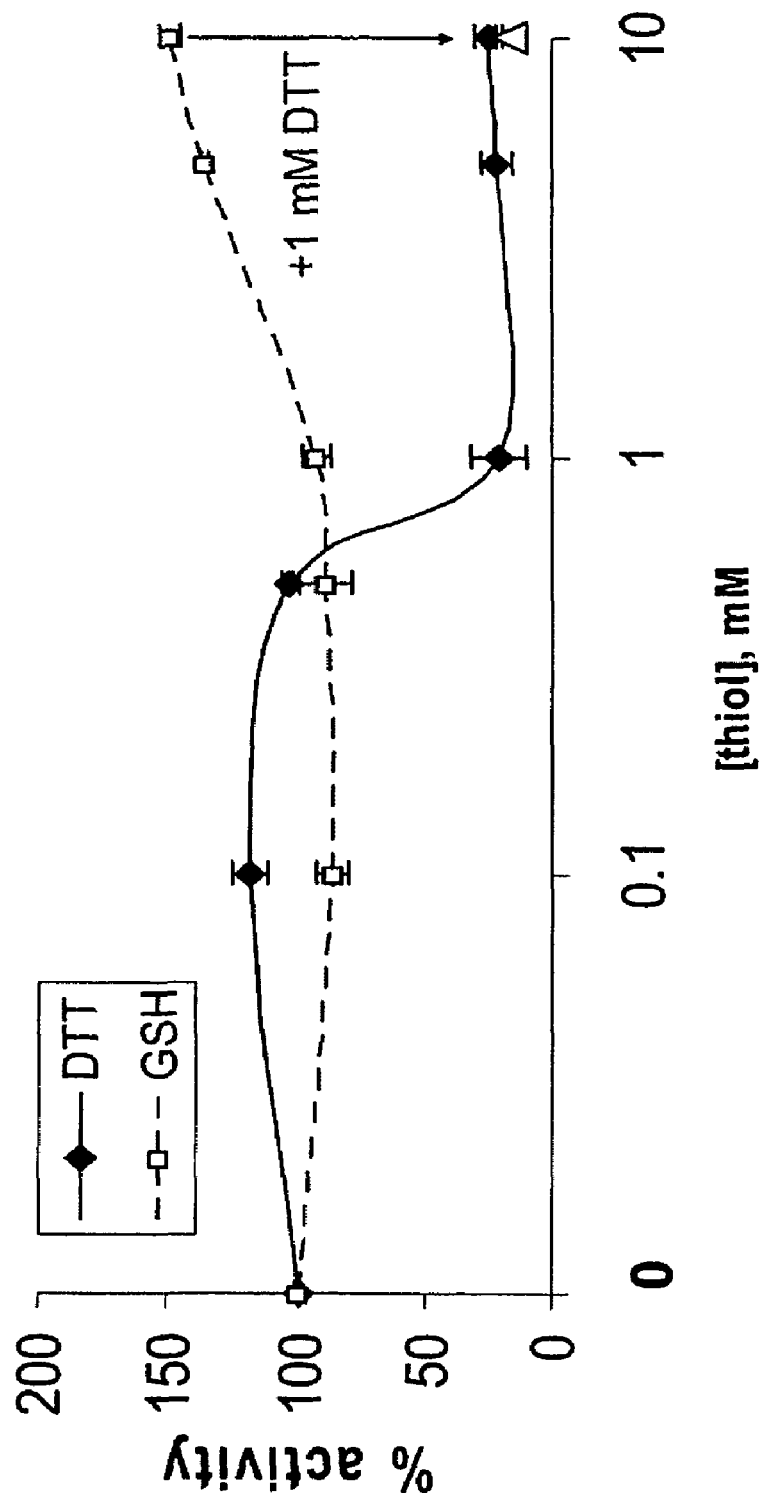

Analysis of various reducing agents indicated that the catalytic properties of the mutant $\alpha\beta^{Cys105}$ enzyme depend on the structure of the thiol used. Concentration-response measurements indicate that an inhibitory effect of DTT was prominent at concentrations higher than 1 mM (FIG. 1B). On the contrary, when glutathione was used as the reducing agent, a slight stimulatory effect of GSH at a concentration above 1 mM was observed. In the presence of GSH, the mutant $\alpha\beta^{Cys105}$ enzyme had a specific activity of up to 2 μmol/min/mg (FIG. 1B). This stimulatory effect was abolished when 1 mM DTT was administered to the GSH-treated enzyme.

The $\alpha\beta^{Cys105}$ Mutant Exhibited a Higher Stimulation by Allosteric Regulators in the Presence of DTT.

A group of structurally related compounds are known to activate the heme competent sGC without changing the absorbance spectrum of the heme moiety. The allosteric regulator YC-1 and structurally related pyrazolopyridine BAY-41-2272 (35, 36) are members of this family. We previously demonstrated that removal of the heme moiety from sGC due to His105→Cys substitution only partially affected the activation of the enzyme by allosteric activators (26). This suggested that activation of sGC by allosteric regulators is both heme-dependent and heme-independent.

We found that YC-1 activation of the $\alpha\beta^{Cys105}$ mutant is affected by DTT. The $\alpha\beta^{Cys105}$ enzyme preserved some activation by YC-1 and was activated up to 3-fold in the presence of DTT (FIG. 2, solid bars). However, in DTT-free conditions the activity of the $\alpha\beta^{Cys105}$ mutant increased only by 30 with YC-1 activation. The extent of YC-1 stimulation of the mutant $\alpha\beta^{Cys105}$ enzyme was not affected by SNP. The wild type enzyme was more efficiently stimulated by YC-1, displaying 11-fold stimulation and a specific activity of 0.15 μmol/min/mg (FIG. 2). SNP enhanced YC-1 dependent stimulation of the wild type enzyme, but not of the mutant $\alpha\beta^{Cys105}$ enzyme. Identical effects on the mutant and wild type enzyme were observed when 2 μM BAY-41-2272 was used instead of 100 μM YC-1 (data not shown), concentrations that are maximally effective (35, 37).

Activation of the Mutant $\alpha\beta^{Cys105}$ Enzyme by Arachidonic Acids.

Some unsaturated fatty acids, such as arachidonic acid, activate wild type sGC independent of nitric oxide and heme (38). The mutant $\alpha\beta^{Cys105}$ enzyme was tested to determine if it preserved these properties. In the absence of DTT, the high activity of the $\alpha\beta^{Cys105}$ enzyme was only modestly stimulated by arachidonic acid (FIG. 3). However, in the presence of DTT, arachidonic acid stimulated the mutant $\alpha\beta^{Cys105}$ enzyme and at 1 mM concentration stimulation was 3.5 fold with a 0.5 (μmol/min/mg activity. Wild type enzyme was also stimulated by arachidonic acid with a maximum 3 fold activation (data not shown), which was not affected by DTT.

Protoporphyrin IX Activates the $\alpha\beta^{Cys105}$ Mutant More Efficiently in the Presence of DTT.

As the $\alpha\beta^{Cys105}$ mutant is heme-deficient, it was decided to test whether the replacement of histidine 105 disrupted only the coordinating bond or induced more profound changes in the heme-binding domain. Protoporphyrin IX (PPIX) has been shown to effectively stimulate sGC (39), especially the heme-deficient sGC (40). In the present investigation, the effect of PPIX on the $\alpha\beta^{Cys105}$ enzyme was tested. In the absence of DTT, 1 μM PPIX stimulated basal activity of the $\alpha\beta^{Cys105}$ mutant only by 80 to a specific activity of 2.2 μmol cGMP/min/mg (FIG. 4). However, in the presence of DTT, the inhibited $\alpha\beta^{Cys105}$ enzyme was more receptive to activation by PPIX and exhibited a 5.4-fold stimulation from 0.13 μmol/min/mg to 0.70 μmol/min/mg activity at 1 μM PPIX. For comparison, PPIX-dependent activation of the heme-containing wild type enzyme resulted in similar activity in the presence or absence of DTT, 0.36 and 0.31 μmol/min/mg, respectively (FIG. 4). Wild type enzyme also showed a higher fold stimulation by PPIX in the presence of DTT, due to a slight decrease in the basal activity in the presence of DTT (0.02 umol/min/mg with DTT vs. 0.05 μmol/min/mg without DTT). Thus, the $\alpha\beta^{Cys105}$ mutant could be activated by PPIX in the presence of DTT, suggesting that the mutation did not irreversibly disturb the conformation of the heme-binding domain.

Partial Restoration of the NO Response After Heme Reconstitution.

Since PPIX activation of the $\alpha\beta^{Cys105}$ mutant suggested that the heme-binding domain retained its properties to bind the protoporphyrin moiety, the $\alpha\beta^{Cys105}$ mutant was tested to determine whether it can be reconstituted with heme. In the absence of DTT, even 1 μM hemin did not confer any sensitivity to SNP (FIG. 5A). Higher concentrations of hemin (10 μM) also did not have any significant effect (data not shown). However, in the presence of 1 mM DTT, the $\alpha\beta^{Cys105}$ mutant partially restored its NO-activation upon addition of hemin. In view of these data, it is suggested that the heme domain of the $\alpha\beta^{Cys105}$ mutant is capable of accepting heme, which is properly oriented and can bind nitric oxide to stimulate the enzyme. However, the complex of the $\alpha\beta^{Cys105}$ enzyme and heme is not stable. The reconstituted enzyme lost its heme and NO activation after the reconstitution buffer was removed by gel filtration (FIG. 5A). NO stimulation was not detected even when the activity was measured immediately after chromatography.

The reconstitution of the $\alpha\beta^{Cys105}$ mutant with heme did not change the extent of activation by YC-1 (FIG. 5B). However, the heme-reconstituted $\alpha\beta^{Cys105}$ mutant demonstrated a greater effect of YC-1 plus NO stimulation (FIG. 5B), exhibiting at least partial restoration of this catalytic property of sGC. Similar data were obtained, when BAY41-2272 was used as the allosteric activator (data not shown).

Catalytic data correlated well with spectroscopic studies of the $\alpha\beta^{Cys105}$ mutant. Addition of reduced hemin to the DTT-treated $\alpha\beta^{Cys105}$ enzyme resulted in the appearance of a Soret peak (FIG. 5C). However, it should be noted that the maximum of the observed Soret peak of the reconstituted $\alpha\beta^{Cys105}$ mutant was at 417 nm vs. 431 nm, characteristic for wild type sGC. Hemin binding to the $\alpha\beta^{Cys105}$ mutant was saturated at 13-fold molar excess of reduced hemin (data not shown), suggesting that interaction between the heme prosthetic group and the enzyme heme pocket is weak. In complete agreement with the activity data (FIG. 5A), the Soret peak of the bound heme disappeared after the reconstituted enzyme was passed through a gel filtration column (FIG. 5C).

No Disulfide Bonds Between $\alpha$ and $\beta$ Subunits of the $\alpha\beta^{Cys105}$ Enzyme.

As the activity of the $\alpha\beta^{Cys105}$ mutant is strongly affected by DTT, a reduction of a putative disulfide bond or a mixed thiol is implicated. A disulfide bond between two subunits of the enzyme, or between two distant cysteine residues of the same subunit will affect the mobility of these subunits on SDS-PAGE under non-reducing conditions. The mobililty of the $\alpha$ and $\beta$ subunits of the $\alpha\beta^{Cys105}$ mutant and wild type enzyme in both reducing and non-reducing SDS-PAGE was compared (FIG. 6). Mobility of both the $\alpha$ and $\beta$ subunits of the $\alpha\beta^{Cys105}$ enzyme was not affected by the treatment with DTT or presence of $\beta$-mercaptoethanol in the SDS-PAGE loading buffer and was no different from the wild type subunits. Thus, no disulfide bonds between the subunits, or distal intramolecular bonds were apparent. In view of these results, it is suggested that sensitivity to DTT is due to the formation of either some close range disulfide bonds, or direct modification of sGC thiols by oxidation or formation of mixed thiols with small molecular thiols, such as cysteine or glutathione.

Intracellular $\alpha\beta^{Cys105}$ Enzyme is Heme-Deficient and More Active than NO-Stimulated Wild Type Enzyme.

As the properties of the $\alpha\beta^{Cys105}$ mutant are affected differently by various thiols, it was decided to test the activity of the $\alpha\beta^{Cys105}$ enzyme in intact cells. Moreover, since the $\alpha\beta^{Cys105}$ mutant could be transiently reconstituted in vitro with heme (FIG. 5), it was also tested whether intracellular conditions are more favorable for the formation of heme competent enzyme than conditions in vitro. Intracellular cGMP accumulation was examined in SF9 cells expressing the $\alpha\beta^{Cys105}$ mutant or the wild type enzymes (FIG. 7). Addition of 1 mM SNP to the wild type SF9/$\alpha\beta$ cells increased the rate of cGMP accumulation almost fourfold from 0.9 nmol/mg/5 min to 3.6 nmol/mg/5 min. It was observed that SNP did not affect the accumulation of cGMP in the Sf9 cells expressing the $\alpha\beta^{Cys105}$ mutant (FIG. 7), thus it is proposed that the intracellular $\alpha\beta^{Cys105}$ mutant is also heme-deficient. However, the basal level of cGMP accumulation in the SF9/$\alpha\beta^{Cys105}$ cells was about ten times higher (33 nmol/mg/5 min) than the rate in NO-activated SF9 cells overexpressing wild type enzyme, although the level of expression was the same (data not shown).

Discussion

Binding of nitric oxide to $Fe^{++}$ in the heme moiety of soluble guanylyl cyclase is the central event leading to the stimulation of sGC. NO induced changes in the interaction between heme and the coordinating histidine 105 residue result in conformational changes which significantly increase the enzyme's specific activity. In previous studies of recombinant wild type human sGC, we (12, 26) and others (41) found that the wild type enzyme displayed a specific activity of ~1.5 µmol/min/mg after exposure to NO. In the present disclosure, an $\alpha\beta^{Cys105}$ mutant variant of the human sGC is described that lacks both the heme moiety and the heme coordinating histidine 105 residue, and which exhibits high constitutive activity similar to activity NO-stimulated wild type enzyme.

The substitution of the histidine 105 residue by a cysteine resulted in a heme deficient sGC, as demonstrated by the lack of a Soret peak characteristic for sGC (FIG. 5C). In the absence of thiols, the $\alpha\beta^{Cys105}$ enzyme has a high specific activity of 1.2±0.3 nmol/mg/min (n=4 independent purifications). The specific activity of the $\alpha\beta^{Cys105}$ mutant varied somewhat with preparation, but this activity was always comparable to the activity of NO-induced wild type enzyme as shown in FIG. 1. High activity of the $\alpha\beta^{Cys105}$ enzyme may be explained by changes in the catalytic center or in the regulatory domain. However, the $\alpha\beta^{Cys105}$ mutant has a GTP-Km similar to previously measured GTP-Km for the wild type enzymes (Table 1) and displays identical to wild type enzyme susceptibility to cystamine inhibition, which is attributed to inhibition of the catalytic function of sGC. These findings suggest that the function of the catalytic center was not affected by the mutation and cannot account for the marked constitutive increase in $\alpha\beta^{Cys105}$ enzyme activity. Since the substituted His 105 is not part of the catalytic domain, but has a demonstrated role in heme coordination, we postulate that the observed $\alpha\beta^{Cys105}$ mutant phenotype reflects changes in the function of the regulatory domain. Wild type enzyme can be stimulated in a NO-independent manner by Protoporphyrin IX, arachidonic acid or with allosteric activators like YC-1 and BAY41-like compounds. Without DTT the activity of $\alpha\beta^{Cys105}$ enzyme was enhanced modestly by NO-independent activators of sGC, such as protoporphyrin IX, arachidonic acid or YC-1 (FIGS. 2, 3 and 4). The mutation did not affect the binding sites of any of the tested NO-independent activators. The exposure of highly active $\alpha\beta^{Cys105}$ enzyme to millimolar concentrations of DTT not only resulted in a 5–7 fold decrease in enzymatic activity, but also restored the mutant's sensitivity to all NO-independent stimulators. This restoration indicates that the mutation did not directly affect the structural elements necessary for the binding or activation by these NO-independent agents. It appears that the $\alpha\beta^{Cys105}$ mutant is purified in a constitutively activated state that is not sensitive to additional stimulation. Such properties are similar to the properties of the NO-stimulated wild type enzyme, which exhibits a blunted response to allosteric regulators at maximal NO activation (37, 42). Thus, it is proposed that the obtained mutant, although heme deficient and without a Histidine 105 residue, achieved a similar conformation as the wild type enzyme stimulated by nitric oxide. Measurements of cGMP accumulation in Sf9 cells (FIG. 7) also demonstrate that the $\alpha\beta^{Cys105}$ enzyme is constitutively highly active.

An earlier report describing the substitution of the Histidine 105 residue of the bovine $\beta$ subunit with phenylalanine (21, 40) clearly demonstrated the heme-coordinating role of the His105 residue. We substituted the heme-coordinating histidine with a cysteine residue, which is also known to coordinate heme, e.g. nitric oxide synthase (43). As summarized in Table 1, the human sGC mutant carrying the $\beta$His105→Cys substitution shares many properties with the bovine sGC with ($\beta$His105→Phe substitution. Both $\alpha\beta^{Phe105}$ and $\alpha\beta^{Cys105}$ enzymes are heme-deficient and do not respond to NO stimulation. However, after heme reconstitution both $\alpha\beta^{Phe105}$ and $\alpha\beta^{Cys105}$ mutants are activated by NO 2.7- (40) and 3.6-fola (FIGS. 5A and B), respectively. The Soret bands for both heme reconstituted mutants were shifted in comparison to the wild type enzyme ($\lambda_{max}$=431 nm). $\alpha\beta^{Cys105}$ enzyme had a Soret peak at 417 nm (FIG. 5C), while the $\alpha\beta^{Phe105}$ sGC had a maximum at 400 nm (40). Spectral differences of these mutants and wild type enzyme are probably due to different heme coordinating residues or lack of such coordination.

Although there are many similarities between these two mutants, there are also some significant differences. $\alpha\beta^{Cys105}$ displayed a high basal activity of 1.2 μmol/min/mg, while the $\alpha\beta^{Phe105}$ had a substantially lower activity of only about 40 nmol/min/mg (40). Even the DTT-inhibited $\alpha\beta^{Cys105}$ had a higher activity than the $\alpha\beta^{Phe105}$ enzyme (Table 1). Another important difference between these mutants is activation by protoporphyrin IX. $\alpha\beta^{Phe105}$ enzyme was able to bind PPIX, as demonstrated by spectral studies, but was not stimulated by PPIX (40). On the contrary, the $\alpha\beta^{Cys105}$ mutant, presented in this report, was stimulated by PPIX, especially after addition of DTT (FIG. 4 and Table 1).

Figure 8:
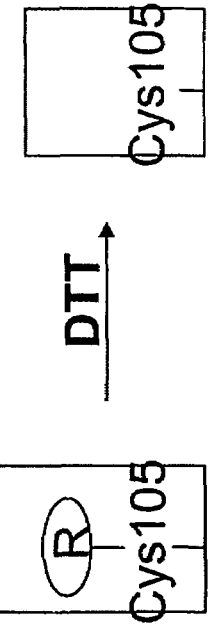
FIG. 8. is a schematic representation of changes in the regulatory domain of wild type and $\alpha\beta^{Cys105}$ sGC.
Figure 8:
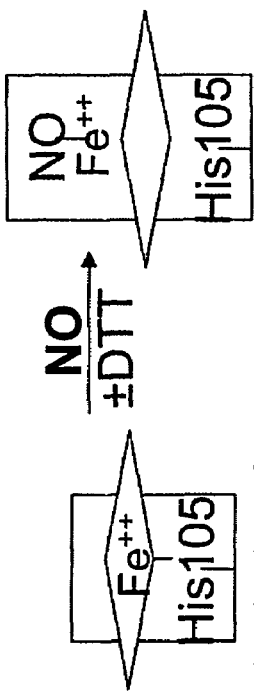

Different responses of these two mutants to protoporphyrin IX provides additional information about the mechanism of sGC activation. A previous model, based on spectroscopic data and supported by the properties of $\alpha\beta^{Phe105}$ enzyme (24, 25, 44), assumed that the release of the coordinating bond between His105 and heme or PPIX insertion to heme-deficient enzyme allows the His105 residue to exert its stimulatory role. This model infers an indispensable role of the Histidine 105 residue for the stimulation of sGC. However, the properties of the $\alpha\beta^{Cys105}$ mutant presented in the instant disclosure indicate that Histidine 105 can be replaced by a structurally unrelated cysteine residue without affecting the ability of sGC to achieve a highly active conformation or be stimulated by protoporphyrin IX. The properties of the $\alpha\beta^{Cys105}$ mutant demonstrate that the His105 does not play a role in stimulating the enzyme. We propose that through the formation of a coordinating bond with heme it retains the regulatory domain in a "restrictive" state, which assures only low basal activity of the enzyme. A schematic representation of changes in the regulatory domain of wild type and $\alpha\beta^{Cys105}$ sGC is shown in FIG. 8. The parallelogram schematically represents the protoporphyrin portion of the heme group, while the box represents the regulatory domain. Changes in the box height represent conformational changes in the regulatory domain. R-putative DTT-sensitive modification of Cys105 or other cysteine residue from the regulatory domain. The binding of NO to heme allows the transition from the "restrictive" conformation of the regulatory domain to a "permissive" conformation, which permits stimulation of the enzyme. Under this model, the histidine 105 residue has an active role before binding of NO, but plays a passive role after NO-induced disruption of the heme-coordinating bond. The $\alpha\beta^{Cys105}$ mutant is constitutively found in such a "permissive" conformation (FIG. 8), which can be inhibited by DTT.

The sensitivity of the $\alpha\beta^{Cys105}$ mutant to DTT is an important feature of this constitutively active mutant. The His105→Cys substitution introduced an additional thiol in the regulatory domain of sGC. DTT-dependent inhibition of the $\alpha\beta^{Cys105}$ enzyme suggests that a thiol modification is essential for constitutively supporting the mutant enzyme in this "permissive" conformation. Analysis of the mobility of $\alpha\beta^{Cys105}$ sGC subunits indicated that no disulfide bonds between α and β subunits or between distant cysteine residues of the same subunit can be detected (FIG. 6). However, this study cannot exclude a close range disulfide bond formation. Cys78 and Cys214 of the β subunit were identified as residues important for heme binding (7) and are, most probably, exposed to the heme pocket and in close proximity to Cys105. Formation of a disulfide bond between these residues might provide necessary structural changes in the regulatory domain to support a "permissive" conformation. Alternatively, Cys105 could form a mixed thiol with a glutathione or cysteine molecule also resulting in formation of a "permissive" conformation. Finally, oxidation of cysteine 105 to sulfenic (—SOH) or sulfinic (—SO$_2$H) acids may be the modification required for the "permissive" conformation. These modifications, schematically represented as "R" in FIG. 8 could be reduced by DTT, resulting in the transition of $\alpha\beta$Cys$^{105}$ regulatory domain from a "permissive" to a "DTT-attenuated" conformation functionally similar to "restrictive" conformation of the wild type sGC.

The constitutively active $\alpha\beta^{Cys105}$ mutant sGC described in this report could be useful to understand the mechanism of sGC activation. Although a large body of evidence exists about changes in the heme moiety of the regulatory domain upon NO induction, the mechanism that couples these events with the stimulation of enzymatic activity in the catalytic center is still not clear. An interaction between the regulatory domain and the catalytic center can be easily envisioned. However, the functional outcome of such interaction is not evident. The catalytic center can be activated by mechanisms similar to Gsa or forskolin activation of adenylyl cyclase (45, 46) or GCAP activation of photoreceptor GC (47). GCAP is known to regulate the function of the retinal membrane-bound guanylyl cyclase (55, 56), and Gsa is known to regulate adenylyl cyclase (57).

In these cases, two cyclase homology domains necessary for the functional catalytic center are brought together by stimulatory molecules. Alternatively, the putative interaction between the regulatory and catalytic domain can have an inhibitory effect, similar to the inhibitory role of the kinase homology domain (KHD) of the membrane guanylyl cyclases with a single transmembrane domain (48). Binding of the ligand to membrane GC results in the relief of inhibition of the catalytic center by KHD (49). In view of the foregoing results and discussion, it is proposed that the Histidine 105 residue of the β subunit plays a crucial role in maintaining the regulatory domain of sGC in a "restrictive" conformation. Substitution of this residue with cysteine mimics the transition of the sGC regulatory domain into a "permissive" conformation. To our knowledge this is the first disclosure of a sGC enzyme that can be maintained in a stimulated state without the addition of stimulatory ligands such as NO or allosteric regulators. Ongoing studies of this mutant are expected to further elucidate the mechanism of sGC stimulation.

Without further elaboration, it is believed that one skilled in the art can, using the description herein, utilize the present invention to its fullest extent. Preferred ways in which the compositions and experimental results described herein may be applied are as follows. These applications are intended to be representative or illustrative of other and various embodiments, and should not be construed as constraining the extent of this disclosure in any way whatsoever.

Identification of Functional Regions Responsible for sGC Regulation

Small deletion probing of sGC regulatory domain in the context of $\beta Cys^{105}$ subunit may permit the identification of functional determinant(s) responsible for sGC regulation. Previously performed deletions (4, 40, 50) or insertions (12) in the N-terminal domains of sGC resulted in enzyme with only basal activity due to the loss of heme moiety. Thus, deletion probing of regulatory determinants based on the wild type enzyme could result in heme-deficient enzyme and limit the application of this approach. The availability of the mutant $\alpha$ $\beta Cys^{105}$ enzyme allows one to perform this analysis without the risk of losing the heme group. Analysis of sGC enzymes carrying $\beta Cys105$ subunit and $\alpha$ subunit containing various deletions in the regulatory domain will permit one to identify the regions in $\alpha$ subunit (if any), which will reduce high specific activity of the mutant $\alpha$ $\beta Cys^{105}$ enzyme to levels similar to the basal activity of the wild type enzyme. For this purpose, the activity of purified $\alpha\beta^{Cys105}$ carrying the mentioned deletions or a cell lysate containing $\alpha\beta^{Cys105}$ enzyme with mentioned deletions will be determined and compared with the activity of the $\alpha\beta^{Cys105}$ enzyme. Analogous studies could be performed for the enzymes carrying, in addition to His105→Cys substitution, various deletions in the regulatory domain in order to identify regulatory determinants in the $\beta$ subunit. Deletions which will only reduce the activity of the $\alpha\beta^{Cys105}$ enzyme, without total loss of ability to synthesize cGMP, will point to elements of sGC enzyme determining the activation process. Identification of these determinants in $\alpha$ and/or $\beta$ subunits will allow one to design new drugs specifically targeting these regulatory determinants. Such studies could be carried in addition to crystallization of the described $\alpha\beta^{Cys105}$ mutant sGC with and without DTT. Comparison of such crystal structures, may be a viable approach to determine structural determinants of sGC stimulation. Deletion probing of the mutant $\alpha\beta^{Cys105}$ enzyme, and crystallographic studies may be carried out using methods and techniques as are known in the art (4, 40, 50).

Use of $\alpha\beta^{Cys105}$ sGC in Inhibitor Screening

The constitutively active mutant may also be a useful reagent to screen for novel inhibitors of sGC. Absence of heme moiety will insure that found inhibitors are not directed towards heme moiety, but towards other structural elements of the enzyme. Screening assays are performed substantially as described in Assay of sGC Activity in Materials and Methods, modified to include an inhibitor, test compound or substance of interest. Alternatively, any other suitable assay method capable of measuring the activity of the $\alpha\beta^{Cys105}$ mutant enzyme may be used, applying the knowledge and techniques that are generally known to those of skill in the art. For example, a screening procedure for identifying a heme-independent inhibitor of soluble guanylyl cyclase includes a) obtaining purified $\alpha\beta^{Cys105}$ mutant soluble guanylyl cyclase enzyme or a cell lysate containing $\alpha\beta^{Cys105}$ mutant soluble guanylyl cyclase enzyme; b) assaying the purified enzyme or cell lysate for formation of cGMP from GTP in the presence of the test compound; and c) assaying the purified enzyme or cell lysate for formation of cGMP from GTP in the absence of the test compound. If desired, steps b) and c) may be carried out in the presence or absence of various activator(s). Finally, the results from the foregoing steps are compared to determine whether the test compound inhibits cGMP production by the purified enzyme or cell lysate.

Use of $\alpha\beta^{Cys105}$ sGC in Activator Screening

The $\alpha\beta^{Cys105}$ mutant enzyme is also useful as a reagent for screening test compounds for heme independent activation of sGC. These assays are also carried out substantially as described above, except that the tests with and without the activator or test compound are compared to determine whether the compound enhances cGMP production by the purified enzyme or cell lysate.

Therapeutic Treatment with $\alpha\beta^{Cys105}$ sGC, or the $\beta$ Subunit

Since sGC is known to be important to the body's regulation of cardiovascular homeostasis, and to play a critical role in neurotransmission, sensory perception, and a variety of pathologies (e.g., high blood pressure, atherosclerosis, septic shock), the $\alpha\beta^{Cys105}$ mutant soluble guanylyl cyclase, or its $\beta^{Cys105}$ subunit, may be employed to initiate, increase and/or sustain the intracellular production of cyclic GMP in a mammalian cell. The procedure may include administering the mutant sGC, or the $\beta^{Cys105}$ subunit, to the mammalian cells. Additionally or alternatively, the procedure may include introducing into the cell an operative gene or coding region of the gene for both $\alpha$ and $\beta^{Cys105}$ subunits or for the mutant subunit alone. The mutant $\beta$ subunit, is then constitutively expressed in the cell and cyclic GMP is produced as a result.

A method of treating or preventing a mammalian pathophysiologic condition associated with cyclic GMP regulation of a cellular process may include causing the constitutive expression of $\alpha\beta^{Cys105}$ mutant sGC in a mammal in need of such treatment or prevention, to initiate, increase and/or sustain intracellular production of cGMP. This may be accomplished by delivering $\alpha\beta^{Cys105}$ mutant sGC enzyme, or the $\beta^{Cys105}$ subunit thereof, to at least one cell of the mammal, preferably a human. Alternatively, the method of treating or preventing a mammalian pathophysiologic condition associated with cyclic GMP regulation of a cellular process may include inhibiting cGMP production by administering an inhibitor of soluble guanylyl cyclase that acts independently of the heme moiety of soluble guanylyl cyclase. Techniques for in vitro and in vivo delivery of proteins are known to those of skill in the art.

Gene Therapy to Provide Constitutive Expression of sGC

Gene delivery of the mutant $\alpha\beta^{Cys105}$ sGC, or the $\beta$ subunit only, may be beneficial in disorders where increased cGMP levels are desired. This may be accomplished by delivering operable genes of $\alpha$ or $\beta^{Cys105}$ sGC subunits, or at least an operable portion of the gene containing the $\beta^{Cys105}$ subunit, into at least one cell in the mammal. Any number of gene delivery methods, which may include, but are not limited to, the administration of naked DNA or cationic lipid-DNA complex (51), virus mediated delivery (52–54). Alternatively, reimplantation of cells from the recipient, or delivery of stem cells, modified to produce the mutant $\alpha\beta^{Cys105}$ sGC could be used to increase the cGMP levels in certain areas of the body.

Pathophysiologic conditions associated with cGMP regulation of a cellular process which are expected to benefit from the above-described treatments include, but are not limited to, angina, chronic heart disease, chronic hypertension (58), thrombosis (59, 60), atherosclerosis (60, 61), congestive heart failure (62, 63), myocardial infarction (64, 65), penile dysfunction (66), tumor or tumor metastasis (67, 68), post-angioplasty complications (69, 70), complications arising from a vein graft operation (71), and septic shock.

TABLE 1

COMPARISON OF SOME PROPERTIES OF $\alpha\beta^{Cys105}$, $\alpha\beta^{Phe105}$ AND WILD TYPE sGC

| | $\alpha\beta^{Cys105}$ | | $\alpha\beta^{Phe105}$ | | Wild Type | |
|---|---|---|---|---|---|---|
| GTP-$K_m$, μM | No DTT | +DTT | ND | | Basal[12,29–31] | NO[12,30–32] |
| | 150 ± 15* | 153 ± 11* | | | 65–448 | 11–134 |
| Heme | No | | No | | Yes | |
| $\lambda_{max}$ of Soret peak, nm | Basal*,# | +NO*,# | Basal | +NO | Basal | +NO |
| | 417 | 400 | 400#,(40) | ND | 431 | 399 |
| Specific activity, μmol/min/mg | Basal* | +NO*,# | Basal[40] | +NO*,(40) | Basal* | +NO* |
| without DTT | 1.2 ± 0.3 | 1.2 ± 0.2 | ND | | 0.05 ± 0.02 | 1.41 ± 0.2 |
| with DTT | 0.12 ± 0.01 | 0.44 ± 0.08 | 0.04 ± 0.03 | 0.11 ± 0.03 | 0.02 ± 0.01 | 1.45 ± 0.1 |
| (fold activation by NO) | (3.6) | | (2.7) | | (72.5) | |
| PPIX activation, fold | No DTT | +DTT | 1[40] | | No DTT | +DTT* |
| | 1.8 | 5.4 | | | 6 | 14 |

*as determined in the present studies;
ND - not reported;
values after heme reconstitution.
Values the $\alpha\beta^{Cys105}$ enzyme are means ±SD of two (GTP-Km) and four (specific activity) independent measurement performed in triplicates.
Values for the $\alpha\beta^{Phe105}$ (specific activity) and the wild type enzyme (GTP-Km) are from cited references.

REFERENCES

The numbered references cited herein are identified as follows:

1. Martin, E., Davis, K., Bian, K., Lee, Y. C., and Murad. F. (2000) *Semin Perinatal* 24 (1), 2–6.
2. Kamisaki, Y., Saheki, S., Nakane, M., Palmieri, J. A., Kuno, T., Chang, B. Y., Waldman, S. A., and Murad, F. (1986) *J Biol Chem* 261 (16), 7236–41.
3. Buechler, W. A. Nakane, M., and Murad, F. (1991) *Biochem Biophys Res Commun* 174 (1), 351–7.
4. Wedel, B., Harteneck, C., Foerster, J., Friebe, A. Schultz. G. and Koesling, D. (1995) *J Biol Chem* 270 (42), 24871–5.
5. Sunahara, R. K., Beuve. A., Tesmer, J. J. Sprang, S. R., Garbers, D. L, and Gilman, A. G. (1998) *J Biol Chem* 273 (26), 16332–8.
6. Gerzer. R., Bohme, E., Hofmann, F., and Schultz, G. (1981) *FEBS Lett* 132 (1), 71–4.
7. Friebe, A., Wedel, B., Harteneck, C. Foerster, J., Schultz, G., and Koesling, D. (1997) *Biochemistry* 36 (6), 1194–8.
8. Ignarro. L. J., Degnan, J. N., Baricos, W. H., Kadowitz, P. J., and Wolin, M. S. (1982) *Biochim Biophys Acta* 718 (1), 49–59.
9. Katsuki, S. Arnold, W., Mittal, C., and Murad, F. (1977) *J Cyclic Nucleotide Res* 3 (1), 23–35.
10. Humbert, P., Niroomand, F., Fischer, G., Mayer, B., Koesling, D., Hinsch, K. D. Gausepohl, H., Frank. R., Schultz, G., and Bohme, E. (1990) *Eur J Biochem* 190 (2), 273–8.
11. Stone, J. R., and Marietta, M. A. (1996) *Biochemistry* 35 (4), 1093–9.
12. Lee, Y. C., Martin, E., and Murad, F. (2000) *Proc Natl Acad Sci USA* 97(20), 10763–8.
13. Stone, J. R., and Marietta, M. A. (1994) *Biochemistry* 33 (18). 5636–40
14. Stone. J. R., Sands, R. H., Dunham, W. R. and Marietta, M. A. (1995) *Biochem Biophys Res Commun* 207 (2), 572–7.
15. Tomita, T., Ogura, T., Tsuyama, S., Imai. Y., and Kitagawa, T. (1997) *Biochemistry* 36 (33), 10155–60.
16. Deinum, G., Stone, J. R., Babcock, G. T., and Marietta, M. A. (1996) *Biochemistry* 35 (5), 1540–7.
17. Kharitonov, V. G., Sharma, V. S., Magde, D., and Koesling, D. (1997) *Biochemistry* 36 (22), 6814–8.
18. Kharitonov, V. G., Russwurm, M., Magde, D., Sharma, V. S. and Koesling. D. (1997) *Biochem Biophys Res Commun* 239 (1), 284–6.
19. Zhao, Y., Brandish, P. E. Ballou. D. P. and Marietta. M. A. (1999) *Proc Natl Acad Sci USA* 96 (26), 14753–8.
20. Bellamy, T. C. Wood, J., and Garthwaite, J. (2002) *Proc Natl Acad Sci USA* 99 (1), 507–10.
21. Wedel, B., Humbert, P., Harteneck, C., Foerster, J., Malkewitz, J., Bohme. E., Schultz, G., and Koesling. D. (1994) *Proc Natl Acad Sci USA* 91 (7), 2592–6.
22. Zhao, Y., Schelvis, J. P., Babcock, G. T., and Marietta, M. A. (1998) *Biochemistry* 37 (13), 4502–9.
23. Zhao, Y., and Marietta, M. A. (1997) *Biochemistry* 36 (50), 15959–64.
24. Koesling. D. and Friebe, A. (1999) *Rev Physiol Biochem Pharmacol* 135, 41–65.
25. Koesling, D. (1999) *Methods* 19 (4), 485–93.
26. Martin, E. Lee, Y. C. and Murad, F. (2001) *Proc NatlAcad Sci USA* 98 (23), 12938–42.
27. Garbers, D. L. (1979) *J Biol Chem* 254 (1), 240–3.
28. Lowry, 0. H., Rosebrough, N. J., Farr, A. L., and Randall, R. J. (1951) *J Biol Chem* 193,265–275.
29. Laemmli, U. K. (1970) *Nature* 227 (259), 680–5.
30. Nakane. M., Hsieh, G., Miller, L. N., Chang, R., Terranova, M. A., Moreland, R. B., Kolasa, T., and Brioni. J. D. (2002) *Int J Impot Res* 14 (2), 121–7.
31. Denninger, J. W., Schelvis, J. P., Brandish. P. E. Zhao, Y., Babcock, G. T., and Marietta, M. A. (2000) *Biochemistry* 39 (14), 4191–8.
32. Friebe. A., Russwurm, M., Mergia, E., and Koesling, D. (1999) *Biochemistry* 38 (46), 15253–7.
33. Kamisaki. Y. Waldman. S. A., and Murad, F. (1986) *Arch Biochem Biophys* 251 (2), 709–14.
34. Rapoport, R. M., and Murad, F. (1988) *Gen Pharmacol* 19 (1), 61–5.
35. Stasch. J. P. Becker, E. M., Alonso-Alija, C. Apeler, H., Dembowsky, K. Feurer, A., Gerzer, R., Minuth, T., Perzbom, E., Pleiss. U. Schroder, H., Schroeder, W., Stahl. E., Steinke, W., Straub, A., and Schramm, M. (2001) *Nature* 410 (6825), 212–5.

36. Stasch, J. P. Alonso-Alija, C., Apeler, H., Dembowsky. K., Feurer, A., Minuth, T., Perzborn, E. Schramm, M., and Straub, A. (2002) *Br J Pharmacol* 135 (2), 333–43.
37. Friebe, A., and Koesling, D. (1998) *Mol Pharmacol* 53 (1), 123–7.
38. Ignarro, L. J., and Wood, K. S. (1987) *Biochim Biophys Acta* 928 (2), 160–70.
39. Ignarro, L. J., Wood, K. S., and Wolin, M. S. (1982) *Proc Natl Acad Sci USA* 79 (9), 2870–3
40. Foerster. J., Harteneck, C., Malkewitz, J., Schultz, G., and Koesling, D. (1996) *Eur J Biochem* 240 (2),380–6.
41. Kosarikov, D. N. Young, P., Uversky, V. N., and Gerber, N. C. (2001) *Arch Biochem Biophys* 388 (2). 185–97.
42. Hoenicka, M., Becker, E. M., Apeler, H. Sirichoke, T., Schroder, H., Gerzer, R., and Stasch. J. P. (1999) *J Mol Mod* 77 (1), 14–23.
43. Stuehr, D. J., and Ikeda-Saito, M. (1992) *J Biol Chem* 267 (29), 20547–50.
44. Sharma, V. S., and Magde, D. (1999) *Methods* 19 (4), 494–505.
45. Tesmer, J. J. Sunahara. R. K., Gilman. A. G., and Sprang. S. R. (1997) *Science* 278 (5345), 1907–16.
46. Sunahara, R. K., Tesmer, J. J., Gilman, A. G., and Sprang, S. R. (1997) *Science* 278 (5345), 1943–7.
47. Olshevskaya. E. V., Ermilov, A. N. and Dizhoor, A. M. (1999) *J Biol Chem* 274 (36), 25583–7.
48. Chinkers, M. and Garbers, D. L. (1989) *Science* 245 (4924). 1392–4.
49. Wedel, B., and Garbers, D. (2001) *Annu Rev Physiol* 63, 215–33.
50. Koglin, M. Stasch, J. P., and Behrends, S. (2002) *Biochem Biophys Res Commun* 292 (4), 1057–62.
51. May, S. and A. Ben-Shaul, Modeling of cationic lipid-DNA complexes. *Curr Med Chem*, 2004. 11(2): p. 151–67.
52. Francis, P. J. and J. T. Stout, Gene therapy and control of angiogenesis. *Ophthalmol Clin North Am*, 2003. 16(4): p. 575–82.
53. Evans, C. H., et al., Osteoarthritis gene therapy. *Gene Ther*, 2004. 11(4): p. 379–89.
54. Sandrin, V., S. J. Russell, and F. L. Cosset, Targeting retroviral and lentiviral vectors. *Curr Top Microbiol Immunol*, 2003. 281: p. 137–78.
55. Koch, K. W., Target recognition of guanylate cyclase by guanylate cyclase-activating proteins. *Adv Exp Med Biol*, 2002. 514: p. 349–60.
56. Newbold, R. J., et al., Guanylate cyclase activating proteins, guanylate cyclase and disease. *Adv Exp Med Biol*, 2002. 514: p. 411–38.
57. Dessauer, C. W., B. A. Posner, and A. G. Gilman, Visualizing signal transduction: receptors, G-proteins, and adenylate cyclases. *Clin Sci (Lond)*, 1996. 91(5): p. 527–37.
58. Abrams, J., Beneficial actions of nitrates in cardiovascular disease. *Am J Cardiol*, 1996. 77(13): p. 31C–7C.
59. Loscalzo, J., Antiplatelet and antithrombotic effects of organic nitrates. *Am J Cardiol*, 1992. 70(8): p. 18B–22B.
60. Vanhoutte, P. M., Endothelial dysfunction and atherosclerosis. *Eur Heart J*. 1997. 18 Suppl E: p. E19–29.
61. Kano, H., et al., Estriol retards and stabilizes atherosclerosis through an NO-mediated system. *Life Sci*, 2002. 71(1): p. 31–42.
62. Takahashi, M., et al., Cyclic GMP production by ANP, BNP, and NO during worsening and improvement of chronic heart failure. *Jpn Heart J*, 2003. 44(5): p. 713–24.
63. Okawa, H., et al., Preischemic infusion of alpha-human atrial natriuretic peptide elicits myoprotective effects against ischemia reperfusion in isolated rat hearts. *Mol Cell Biochem*, 2003. 248(1–2): p. 171–7.
64. Torfgard, K. E. and J. Ahlner, Mechanisms of action of nitrates. *Cardiovasc Drugs Ther*, 1994. 8(5): p. 701–17.
65. Zusman, R. M., et al., Overall cardiovascular profile of sildenafil citrate. *Am J Cardiol*, 1999. 83(5A): p. 35C–44C.
66. Nakane, M., Soluble guanylyl cyclase: physiological role as an NO receptor and the potential molecular target for therapeutic application. *Clin Chem Lab Med*, 2003. 41(7): p. 865–70.
67. Gallo, O., et al., Role of nitric oxide in angiogenesis and tumor progression in head and neck cancer. *J Natl Cancer Inst*, 1998. 90(8): p. 587–96.
68. Spoto, G., et al., Cyclic guanosine monophosphate phosphodiesterase activity in human gingival carcinoma. *J Oral Pathol Med*, 2003. 32(4): p. 189–94.
69. Sinnaeve, P., et al., Overexpression of a constitutively active protein kinase G mutant reduces neointima formation and in-stent restenosis. *Circulation*, 2002. 105(24): p. 2911–6.
70. Do, Y. S., et al., In-stent restenosis limitation with stent-based controlled-release nitric oxide: initial results in rabbits. *Radiology*, 2004. 230(2): p. 377–82.
71. Kibbe, M. R., et al., Optimization of ex vivo inducible nitric oxide synthase gene transfer to vein grafts. *Surgery*, 1999. 126(2): p.323–9

Definitions/Abbreviations

The abbreviations used herein are: sGC, soluble guanylyl cyclase; SNP, Sodium nitroprusside; YC-1,3-(5'-Hydroxymethyl-2'furyl)-1-benzyl-indazole; cGMP, cyclic guanosine 3',5'-monophosphate. IBMX, 3-isobutyM-methylxanthine, NOC-7, 3-(2-hydroxyl-1-methyl-2nitrosohydrazino)-N-methyl-1-propanamine; BAY 41-2272, 5-cyclopropyl-2-[1-(2-fluoro-benzyl)-1H-pyrazolo[3,4-b]pyridin-3-yl]-pyrimidin-4-ylamine; PPIX, protoporphyrin IX; DMSO, dimethylsulfoxide; KHD, kinase homology domain. GCAP, guanylyl cyclase activating proteins; Gsa, alpha subunit of one of G-proteins (Gs isoform).

While the preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. The disclosures of all publications, patents and patent applications cited herein are incorporated by reference to the extent that they describe methods and materials not expressly set forth herein.

What is claimed is:

1. A method of screening a substance of interest for heme independent modulation of enzymatic activity of soluble guanylyl cyclase (sGC) comprising:
  a) obtaining purified $\alpha\beta^{Cys105}$ mutant soluble guanylyl cyclase enzyme or a cell lysate containing $\alpha\beta^{Cys105}$ mutant soluble guanylyl cyclase enzyme;
  b) determining activity of said purified enzyme or cell lysate for forming cGMP from GTP in a reaction medium in the presence of said substance;
  c) determining activity of said purified enzyme or cell lysate for forming cGMP from GTP in a reaction medium in the absence of said substance;

optionally, d) carrying out steps b) and c) in the presence of an activator other than said substance;

e) comparing the determinations horn b) and c), and, d), if present, to yield a comparison result; and f) assessing the activity of said substance to modulate cGMP production by said purified enzyme or cell lysate from the value of said comparison result, wherein increased or decreased formation of cGMP in the presence of said substance indicates that said substance is active for modulating heme independent cGMP production.

2. The method of claim 1 wherein increased formation of cGMP in the presence of said substance indicates that said substance enhances cGMP production by said purified enzyme or cell lysate.

3. The method of claim 2 wherein increased formation of cGMP in the presence of said substance indicates that said substance affects a structural element of the sGC enzyme other than a heme moiety to cause enhancement of sGC activity.

4. The method of claim 1 wherein decreased formation of cGMP in the presence of said substance indicates that said substance inhibits cGMP production by said purified enzyme or cell lysate.

5. The method of claim 4 wherein said decreased formation of cGMP in the presence of said substance indicates that said substance affects a structural element of the sGC enzyme other than a heme moiety to cause inhibition of sGC activity.

6. The method of claim 1 wherein step d) is included and said activator comprises DTT.

* * * * *